(12) United States Patent
Hennequin

(10) Patent No.: US 7,173,136 B2
(45) Date of Patent: Feb. 6, 2007

(54) 3-CYANO-QUINOLINE DERIVATIVES

(75) Inventor: Laurent Francois Andre Hennequin, Reims (FR)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 10/532,958

(22) PCT Filed: Oct. 28, 2003

(86) PCT No.: PCT/GB03/04661

§ 371 (c)(1),
(2), (4) Date: Apr. 27, 2005

(87) PCT Pub. No.: WO2004/041811

PCT Pub. Date: May 21, 2004

(65) Prior Publication Data

US 2005/0282856 A1 Dec. 22, 2005

(30) Foreign Application Priority Data

Nov. 2, 2002 (GB) ................................. 0225579.2

(51) Int. Cl.
*C07D 215/38* (2006.01)
*C07D 215/44* (2006.01)
(52) U.S. Cl. ...................................... 546/153; 546/159
(58) Field of Classification Search ................. 514/311, 514/312, 313; 546/153, 159
See application file for complete search history.

(56) References Cited

U.S. PATENT DOCUMENTS

| | | | |
|---|---|---|---|
| 3,376,195 A | 4/1968 | Allais et al. ................. 514/310 |
| 3,936,461 A | 2/1976 | Schwender et al. ........... 546/90 |
| 4,421,920 A | 12/1983 | Baudouin et al. ........... 546/163 |
| 5,145,843 A | 9/1992 | Arnold et al. ............... 514/63 |
| 5,240,940 A | 8/1993 | Arnold et al. ............... 514/312 |
| 5,409,930 A | 4/1995 | Spada et al. ................. 514/248 |
| 5,506,235 A | 4/1996 | Moyer et al. ................. 514/293 |
| 5,576,322 A | 11/1996 | Takase et al. ........... 514/266.22 |
| 5,650,415 A | 7/1997 | Tang et al. ................. 514/312 |
| 5,656,643 A | 8/1997 | Spada et al. ................. 514/312 |
| 5,693,652 A | 12/1997 | Takase et al. ............... 514/322 |
| 5,801,180 A | 9/1998 | Takase et al. ........... 514/266.24 |
| RE36,256 E | 7/1999 | Spada et al. ................. 514/249 |
| 6,002,008 A | 12/1999 | Wissner et al. .............. 546/160 |
| 6,143,764 A | 11/2000 | Kubo et al. .................. 514/312 |
| 6,225,318 B1 * | 5/2001 | Sobolov-Jaynes et al. ......................... 514/266.2 |
| 6,391,874 B1 | 5/2002 | Cockerill et al. ......... 514/233.5 |
| 6,630,489 B1 | 10/2003 | Crawley ..................... 514/311 |
| 6,638,945 B1 | 10/2003 | Gibson ....................... 514/311 |
| 6,713,485 B2 | 3/2004 | Carter et al. ........... 514/266.24 |
| 6,727,256 B1 | 4/2004 | Carter et al. ................. 544/279 |
| 6,809,106 B1 | 10/2004 | Gibson ....................... 514/311 |
| 6,828,320 B2 | 12/2004 | Cockerill et al. ......... 514/233.5 |
| 2002/0147205 A1 | 10/2002 | Carter et al. ........... 514/266.24 |
| 2002/0147214 A1 | 10/2002 | Cockerill et al. ........... 514/311 |
| 2003/0176451 A1 | 9/2003 | Carter et al. ........... 514/264.11 |
| 2004/0029898 A1 | 2/2004 | Boyle et al. ................. 514/256 |
| 2004/0034046 A1 | 2/2004 | Hennequin et al. ..... 514/266.24 |
| 2004/0138240 A1 | 7/2004 | Ple ......................... 514/266.24 |
| 2004/0214841 A1 | 10/2004 | Hennequin et al. ....... 514/266.2 |
| 2005/0009867 A1 | 1/2005 | Hennequin ................. 514/312 |
| 2005/0101630 A1 | 5/2005 | Boyle et al. ................. 514/312 |
| 2005/0130996 A1 | 6/2005 | Carter et al. ........... 514/266.24 |

FOREIGN PATENT DOCUMENTS

| | | |
|---|---|---|
| EP | 0326330 | 8/1989 |
| EP | 0607439 | 7/1994 |
| EP | 0837063 | 4/1998 |
| FR | 2077455 | 9/1969 |
| WO | WO 93/03030 | 2/1993 |
| WO | WO 96/09294 | 3/1996 |

(Continued)

OTHER PUBLICATIONS

U.S. Appl. No. 09/959,813, filed Nov. 8, 2001, Francis Thomas Boyle et al.

(Continued)

*Primary Examiner*—D. Margaret Seaman
(74) *Attorney, Agent, or Firm*—Morgan Lewis & Bockius LLP

(57) ABSTRACT

The invention concerns quinoline derivatives of Formula (I) wherein each of $Z^1$, m, $R^1$, n, $R^3$, $Z^2$ and $R^{14}$ have any of the meanings defined hereinbefore in the description; processes for their preparation, pharmaceutical compositions containing them and their use in the manufacture of a medicament for use as an anti-invasive or anti-proliferative agent in the containment and/or treatment of solid tumour disease

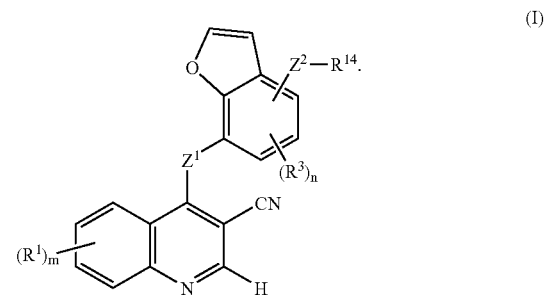

(I)

9 Claims, No Drawings

FOREIGN PATENT DOCUMENTS

| | | |
|---|---|---|
| WO | WO 97/03069 | 1/1997 |
| WO | WO 97/17329 | 5/1997 |
| WO | WO 98/02434 | 1/1998 |
| WO | 98/13350 | 4/1998 |
| WO | WO 98/13350 | 4/1998 |
| WO | 98/43960 | 10/1998 |
| WO | WO 98/43960 | 10/1998 |
| WO | WO 99/35146 | 7/1999 |
| WO | WO 00/18761 | 4/2000 |
| WO | 00/68201 | 11/2000 |
| WO | WO 00/68199 | 11/2000 |
| WO | WO 00/68200 | 11/2000 |
| WO | WO 00/68201 | 11/2000 |
| WO | WO 01/94341 | 12/2001 |
| WO | 0216352 | 2/2002 |
| WO | WO 02/16352 | 2/2002 |
| WO | WO 02/36570 | 5/2002 |
| WO | WO 02/44166 | 6/2002 |
| WO | WO 02/085895 | 10/2002 |
| WO | WO 03/008409 | 1/2003 |
| WO | 03047584 | 6/2003 |
| WO | 03048159 | 6/2003 |
| WO | WO 03/047582 | 6/2003 |
| WO | WO 03/047583 | 6/2003 |
| WO | WO 03/047584 | 6/2003 |
| WO | WO 03/047585 | 6/2003 |
| WO | WO 03/048159 | 6/2003 |
| WO | WO 03/053960 | 7/2003 |
| WO | WO 04/004732 | 1/2004 |
| WO | WO 04/005284 | 1/2004 |

OTHER PUBLICATIONS

U.S. Appl. No. 09/959,005, filed Oct. 17, 2001, Keith Hopkinson Gibson.
U.S. Appl. No. 09/959,434, filed Oct. 25, 2001, Keith Hopkinson Gibson.
U.S. Appl. No. 10/275,382, filed Nov. 5, 2002, Laurent Francois Andre Hennequin et al.
U.S. Appl. No. 10/344,678, filed Feb. 14, 2003, Laurent Francois Andre Hennequin et al.
U.S. Appl. No. 10/415,812, filed May 2, 2003, Francis Thomas Boyle et al.
U.S. Appl. No. 10/415,813, filed May 2, 2005, Francis Thomas Boyle et al.
U.S. Appl. No. 10/475,016, filed Oct. 16, 2003, Patrick Ple.
U.S. Appl. No. 10/483,782, filed Aug. 11, 2004, Laurent Francois Andre Hennequin.
U.S. Appl. No. 10/520,468, filed Jan. 7, 2005, Laurent Francois Andre Hennequin et al.
U.S. Appl. No. 10/520,266, filed Jan. 6, 2005, Laurent Francois Andre Hennequin et al.

* cited by examiner

3-CYANO-QUINOLINE DERIVATIVES

The invention concerns certain novel quinoline derivatives, or pharmaceutically-acceptable salts thereof, which possess anti-tumour activity and are accordingly useful in methods of treatment of the human or animal body. The invention also concerns processes for the manufacture of said quinoline derivatives, pharmaceutical compositions containing them and their use in therapeutic methods, for example in the manufacture of medicaments for use in the prevention or treatment of solid tumour disease in a warm-blooded animal such as man.

Many of the current treatment regimes for cell proliferation diseases such as psoriasis and cancer utilise compounds which inhibit DNA synthesis. Such compounds are toxic to cells generally but their toxic effect on rapidly dividing cells such as tumour cells can be beneficial. Alternative approaches to anti-tumour agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*. 1986, 1, 91). Oncogenes give rise to the production of peptides which are receptors for growth factors. Activation of the growth factor receptor complex subsequently leads to an increase in cell proliferation. Oncogenes often encode abnormal versions of signal pathway components, such as receptor tyrosine kinases, serine-threonine kinases, or downstream signaling molecules such as the ras genes. The ras genes code for closely related small guanine nucleotide binding proteins which hydrolyse bound guanosine triphosphate (GTP) to guanosine diphosphate (GDP). Ras proteins are active in promoting cell growth and transformation when they are bound to GTP and inactive when they are bound to GDP. Transforming mutants of p21ras are defective in their GTPase activity and hence remain in the active GTP bound state. The ras oncogene is known to play an integral role in certain cancers and has been found to contribute to the formation of over 20% of all cases of human cancer.

When activated by ligand such as a growth factor, cell surface receptors which are coupled to the mitogenic response can initiate a chain of reactions which leads to the activation of guanine nucleotide exchange activity on ras proteins. When ras protein is in its active GTP-bound state, a number of other proteins interact directly with ras at the plasma membrane resulting in signal transmission through several distinct pathways. The best characterised effector protein is the product of the raf proto-oncogene. The interaction of raf and ras is a key regulatory step in the control of cell proliferation. Ras-mediated activation of the raf serine-threonine kinase in turn activates the dual-specificity MEK (MEK1 and MEK2), which is the immediate upstream activator of mitogen activated protein kinase (MAPKs known as extracellular signal regulated protein kinases or ERK1 and ERK2). To date, no substrates of MEK other than MAPK have been identified, though recent reports indicate that MEK may also be activated by other upstream signal proteins such as MEKK1 and Cot/Tpl-2. Activated MAPK translocates and accumulates in the nucleus, where it can phosphorylate and activate transcription factors such as Elk-1 and Sap1a, leading to the enhanced expression of genes such as c-fos.

The ras-dependent raf-MEK-MAPK cascade is one of the key signalling pathways responsible for transmitting and amplifying mitogenic signals from cell surface to the nucleus resulting in changes in gene expression and cell fate. This ubiquitous pathway appears essential for normal cell proliferation and constitutive activation of this pathway is sufficient to induce cellular transformation. Transforming mutants of p21ras are constitutively active, resulting in raf, MEK and MAPK activity and cell transformation. Inhibition of MEK activity using either antisense raf a dominant negative MEK mutant or the selective inhibitor PD098059 has been shown to block the growth and morphological transformation of ras-transformed fibroblasts.

The mechanism of activation of raf, MEK and MAPK is through phosphorylation on specific serine, threonine or tyrosine residues. Activated raf and other kinases phosphorylate MEK1 on S218 and S222 and MEK2 on S222 and S226. This results in MEK activation and subsequent phosphorylation and activation of ERK1 on T190 and Y192 and ERK2 on T183 and Y185 by the dual specificity MEKs. Whilst MEK can be activated by a number of protein kinases, and active MAPKs phosphorylate and activate a number of substrate proteins including transcription factors and other protein kinases, MEKs appear specific and sole activators of MAPKs and could act as a focal point for cross-cascade regulation. MEK1 and MEK2 isoforms show unusual specificity and also contain a proline-rich insert between catalytic subdomains IX and X which is not present in any of the other known MEK family members. These differences between MEK and other protein kinases, together with the known role of MEK (MEK 1, MEK 2) and, more recently MEK 5, in proliferative signalling suggest it may be possible to discover and employ selective MEK inhibitors as therapeutic agents for use in proliferative disease.

Accordingly, it has been recognised that an inhibitor of the MAPK kinase pathway should be of value as an anti-proliferative agent for use in the containment and/or treatment of solid tumour disease.

It is also known that several oncogenes encode tyrosine kinase enzymes and that certain growth factor receptors are also tyrosine kinase enzymes (Yarden et at., *Ann. Rev. Biochem.*, 1988, 57, 443; Larsen et al., *Ann. Reports in Med. Chem.*, 1989, Chpt. 13). The first group of tyrosine kinases to be identified arose from such viral oncogenes, for example pp60$^{v-Src}$ tyrosine kinase (otherwise known as v-Src), and the corresponding tyrosine kinases in normal cells, for example pp60$^{c-Src}$ tyrosine kinase (otherwise known as c-Src).

Receptor tyrosine kinases are important in the transmission of biochemical signals which initiate cell replication. Some of them are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research* 1993, 60, 43–73) based on families of growth factors which bind to different receptor tyrosine kinases. The classification includes Class I receptor tyrosine kinases comprising the EGF family of receptor tyrosine kinases such as the EGF, TGFα, Neu and erbB receptors, Class II receptor tyrosine kinases comprising the insulin family of receptor tyrosine kinases such as the insulin and IGFI receptors and insulin-related receptor (IRR) and Class III receptor tyrosine kinases comprising the platelet-derived growth factor (PDGF) family of receptor tyrosine kinases such as the PDGFα, PDGFβ and colony-stimulating factor 1 (CSF1) receptors.

It is also known that certain tyrosine kinases belong to the class of non-receptor tyrosine kinases which are located intracellularly and are involved in the transmission of biochemical signals such as those that influence tumour cell motility, dissemination and invasiveness and subsequently metastatic tumour growth (Ullrich et al., *Cell* 1990, 61, 203–212, Bolen et al., *FASEB J.*, 1992, 6, 3403–3409, Brickell et al., *Critical Reviews in Oncogenesis*, 1992, 3, 401–406, Bohlen et al., *Oncogene*, 1993, 8, 2025–2031, Courtneidge et al., *Semin. Cancer Biol.*, 1994, 5, 239–246, Lauffenburger et al., *Cell*, 1996, 4, 359–369, Hanks et al., *BioEssays*, 1996, 19, 137–145, Parsons et al., *Current Opinion in Cell Biology*, 1997, 9, 187–192, Brown et al., *Biochimica et Biophysica Acta*, 1996, 1287, 121–149 and Schlaepfer et al., *Progress in Biophysics and Molecular Biology*, 1999, 71, 435–478). Various classes of non-receptor tyrosine kinases are known including the Src family such as the Src, Lyn and Yes tyrosine kinases, the Abl family such as Abl and Arg and the Jak family such as Jak 1 and Tyk 2.

It is known that the Src family of non-receptor tyrosine kinases are highly regulated in normal cells and in the absence of extracellular stimuli are maintained in an inactive conformation. However, some Src family members, for example c-Src tyrosine kinase, are frequently significantly activated (when compared to normal cell levels) in common human cancers such as gastrointestinal cancer, for example colon, rectal and stomach cancer (Cartwright et al., *Proc. Natl. Acad. Sci. USA*, 1990, 87, 558–562 and Mao et al., *Oncogene*, 1997, 15, 3083–3090), and breast cancer (Muthuswamy et al., *Oncogene*, 1995, 11, 1801–1810). The Src family of non-receptor tyrosine kinases has also been located in other common human cancers such as non-small cell lung cancers (NSCLCs) including adenocarcinomas and squamous cell cancer of the lung (Mazurenko et al. *European Journal of Cancer*, 1992, 28, 372–7), bladder cancer (Fanning et al., *Cancer Research*. 1992, 52, 1457–62), oesophageal cancer (Jankowski et al., *Gut*, 1992, 33, 1033–8), cancer of the prostate, ovarian cancer (Wiener et al., *Clin. Cancer Research*, 1999, 5, 2164–70) and pancreatic cancer Lutz et al., *Biochem. and Biolphys. Res. Comm.*, 1998, 243, 503–8). As further human tumour tissues are tested for the Src family of non-receptor tyrosine kinases it is expected that its widespread prevalence will be established.

It is further known that the predominant role of c-Src non-receptor tyrosine kinase is to regulate the assembly of focal adhesion complexes through interaction with a number of cytoplasmic proteins including, for example, focal adhesion kinase and paxillin. In addition c-Src is coupled to signalling pathways that regulate the actin cytoskeleton which facilitates cell motility. Likewise, important roles are played by the c-Src, c-Yes and c-Fyn non-receptor tyrosine kinases in integrin mediated signalling and in disrupting cadherin-dependent cell-cell junctions (Owens et al., *Molecular Biology of the Cell*, 2000, 11, 51–64 and Klinghoffer et al., *EMBO Journal*, 1999, 18, 2459–2471). Cellular motility is necessarily required for a localised tumour to progress through the stages of dissemination into the blood stream, invasion of other tissues and initiation of metastatic tumour growth. For example, colon tumour progression from localised to disseminated, invasive metastatic disease has been correlated with c-Src non-receptor tyrosine kinase activity (Brunton et al., *Oncogene*, 1997, 14, 283–293, Fincham et al, *EMBO J,* 1998, 17, 81–92 and Verbeek et al., *Exp. Cell Research*, 1999, 248, 531–537).

Accordingly it has been recognised that an inhibitor of such non-receptor tyrosine kinases should be of value as a selective inhibitor of the motility of tumour cells and as a selective inhibitor of the dissemination and invasiveness of mammalian cancer cells leading to inhibition of metastatic tumour growth. In particular an inhibitor of such non-receptor tyrosine kinases should be of value as an anti-invasive agent for use in the containment and/or treatment of solid tumour disease.

We have now found that surprisingly certain quinoline derivatives possess potent anti-tumour activity. It is believed that the compounds disclosed in the present invention provide an anti-tumour effect by way of inhibition of MEK enzymes that are involved in the MAPK kinase pathway and/or by way of inhibition of one or more of the non-receptor tyrosine-specific protein kinases that are involved in the signal transduction steps which lead to the invasiveness and migratory ability of metastasising tumour cells. In particular, it is believed that the compounds of the present invention provide an anti-tumour effect by inhibition of one or more of the MEK enzymes and/or by way of inhibition of the Src family of non-receptor tyrosine kinases, for example by inhibition of one or more of c-Src, c-Yes and c-Fyn. It is also known that c-Src non-receptor tyrosine kinase enzyme is involved in the control of osteoclast-driven bone resorption (Soriano et al., *Cell,* 1991, 64, 693–702; Boyce et al., *J. Clin. Invest.*, 1992, 90, 1622–1627; Yoneda et al., *J. Clin. Invest*, 1993, 21, 2791–2795 and Missbach et al., *Bone,* 1999, 24,437–49). An inhibitor of c-Src non-receptor tyrosine kinase is therefore of value in the prevention and treatment of bone diseases such as osteoporosis, Paget's disease, metastatic disease in bone and tumour-induced hypercalcaemia.

The compounds of the present invention are also useful in inhibiting the uncontrolled cellular proliferation which arises from various non-malignant diseases such as inflammatory diseases (for example rheumatoid arthritis and inflammatory bowel disease), fibrotic diseases (for example hepatic cirrhosis and lung fibrosis), glomerulonephritis, multiple sclerosis, psoriasis, hypersensitivity reactions of the skin, blood vessel diseases (for example atherosclerosis and restenosis), allergic asthma, insulin-dependent diabetes, diabetic retinopathy and diabetic nephropathy.

The compounds of the invention may possess inhibitory acitivity against the MEK enzymes that are involved in the MAPK kinase pathway. They may also possess an inhibitory activity against the Src family of non-receptor tyrosine kinases. Generally the compounds of the present invention may also possess potent inhibitory activity against the Src family of non-receptor tyrosine kinases, for example by inhibition of c-Src and/or c-Yes, whilst possessing less potent inhibitory activity against other tyrosine kinase enzymes such as the receptor tyrosine kinases, for example EGF receptor tyrosine kinase and/or VEGF receptor tyrosine kinase.

It is stated in International Patent Application WO 98/43960 that a range of 3-cyanoquinoline derivatives are useful in the treatment of cancer. Certain of the compounds are stated to be inhibitors of EGF receptor tyrosine kinase, others are stated to be inhibitors of the mitogen-activated protein kinase (MAPK) pathway and others are stated to be inhibitors of growth factors such as vascular endothelial growth factor (VEGF). There is no disclosure therein of any 4-benzofuranylamino-3-cyanoquinoline derivatives.

It is stated in International Patent Application WO 00/68201 that a range of 3-cyanoquinoline derivatives are also useful in the treatment of cancer. Certain of the compounds are stated to be inhibitors of MEK, a MAPK kinase. There is no disclosure therein of any 4-benzofuranylamino-3-cyanoquinoline derivatives.

It is also stated in International Patent Application WO 00/18761 that a range of 3-cyanoquinoline derivatives are also useful in the treatment of cancer. Certain of the compounds are stated to be inhibitors of MEK, a MAPK kinase. There is no disclosure therein of any 4-benzofuranylamino-3-cyanoquinoline derivatives.

According to one aspect of the invention there is provided a quinoline derivative of the Formula I

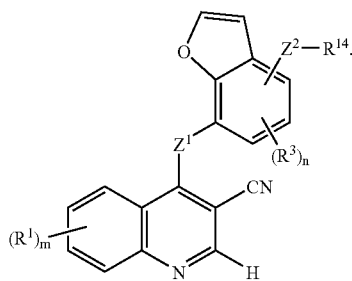

I wherein $Z^1$ is an O, S, SO, $SO_2$, $N(R^2)$ or $C(R^2)_2$ group, wherein each $R^2$ group, which may be the same or different, is hydrogen or (1–6C)alkyl;

m is 0, 1, 2, 3 or 4;

each $R^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

$Q^1$-$X^1$— wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenedioxy, and wherein adjacent carbon atoms in any (2–6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH═CH and C≡C wherein $R^5$ is hydrogen or (1–6C)alkyl or, when the inserted group is $N(R^5)$, $R^5$ may also be (2–6C)alkanoyl, and wherein any CH₂═CH— or HC≡C— group within a $R^1$ substituent optionally bears at the terminal CH₂═ or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl, di-[(1–6C)alkyl]amino-(1–6C)alkyl or from a group of the formula:

$Q^2$-$X^2$— wherein $X^2$ is a direct bond or is selected from CO and $N(R^6)CO$, wherein $R^6$ is hydrogen or (1–6C)alkyl, and $Q^2$ is aryl, aryl-(1–6C)alkyl, heteroaryl, heteroaryl-(1–6C)alkyl, heterocyclyl or heterocyclyl-(1–6C)alkyl, and wherein any CH, CH₂ or CH₃ group within a $R^1$ substituent optionally bears on each said CH, CH₂ or CH₃ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

—$X^3$-$Q^3$ wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

—$X^4$—$R^8$ wherein $X^4$ is a direct bond or is selected from O and $N(R^9)$, wherein $R^9$ is hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl or from a group of the formula:

—$X^5$-$Q^4$ wherein $X^5$ is a direct bond or is selected from O, $N(R^{10})$ and CO, wherein $R^{10}$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and wherein any heterocyclyl group within a substituent on $R^1$ optionally bears 1 or 2 oxo or thioxo substituents;

n is 0, 1, 2 or 3;

each $R^3$ group is halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

wherein $X^6$ is a direct bond or is selected from O and $N(R^{12})$, wherein $R^{12}$ is hydrogen or (1–6C)alkyl, and $R^{11}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl;

$Z^2$ is a C≡C or $C(R^{13})$═$C(R^{13})$ group, wherein each $R^{13}$ group, which may be the same or different, is hydrogen or (1–6C)alkyl; and $R^{14}$ is selected from halogeno, cyano, isocyano, formyl, carboxy, carbamoyl, (2–8C)alkenyl, (2–8C)alkynyl, (1–6C)alkoxycarbonyl, N-(1–6C)alkylcarbamoyl, N,N-di-[(1–6C)alkyl]carbamoyl, (2–6C)alkanoyl, N-(1–6C)alkylsulphamoyl, N,N-di-[(1–6C)alkyl]sulphamoyl, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6-C)alkyl, (2–6C)alkanoylamino-(1–6C)alkyl, (1–6C)alkoxycarbonylamino-(1–6C)alkyl or from a group of the formula:

wherein $X^7$ is a direct bond or is selected from CO, $CH(OR^{15})$, $CON(R^{15})$ or $SO_2N(R^{15})$, wherein $R^{15}$ is hydrogen or (1–6C)alkyl, and $Q^5$ is aryl, aryl-(1–6C)alkyl, (3–7C)cycloalkyl, (3–7C)cycloalkyl-(1–6C)alkyl, heteroaryl, heteroaryl-(1–6C)alkyl, heterocyclyl or heterocyclyl-(1–6C)alkyl, and wherein any CH, $CH_2$ or $CH_3$ group within a $R^{14}$ substituent optionally bears on each said CH, $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

wherein $X^8$ is a direct bond or is selected from O, S, SO, $SO_2$, $N(R^{16})$, CO, $CH(OR^{16})$, $CON(R^{16})$, $N(R^{16})CO$, $SO_2N(R^{16})$, $N(R^{16})SO_2$, $C(R^{16})_2O$, $C(R^{16})_2S$ and $N(R^{16})C(R^{16})_2$, wherein $R^{16}$ is hydrogen or (1–6C)alkyl, and $Q^6$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl(1-C)alkyl, and wherein any aryl, heteroaryl or heterocyclyl group within a substituent on $R^{14}$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

wherein $X^9$ is a direct bond or is selected from O and $N(R^{18})$, wherein $R^{18}$ is hydrogen or (1–6C)alkyl, and $R^{17}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1-C)alkoxycarbonylamino-(1–6C)alkyl, or from a group of the formula:

wherein $X^{10}$ is a direct bond or is selected from O, $N(R^{19})$ and CO, wherein $R^{19}$ is hydrogen or (1–6C)alkyl and $Q^7$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and wherein any heterocyclyl group within a substituent on $R^{14}$ optionally bears 1 or 2 oxo or thioxo substituents;

or a pharmaceutically-acceptable salt thereof.

In this specification the generic term "alkyl" includes both straight-chain and branched-chain alkyl groups such as propyl, isopropyl and tert-butyl, and also (3–7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1–6C)alkoxy includes methoxy, ethoxy, cyclopropyloxy and cyclopentyloxy, (1–6C)alkylamino includes methylamino, ethylamino, cyclobutylamino and cyclohexylamino, and di-[(1–6Calkyl]amino includes dimethylamino, diethylamino, N-cyclobutyl-N-methylamino and N-cyclohexyl-N-ethylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the 'Q' groups ($Q^1$ to $Q^7$) when it is aryl or for the aryl group within a 'Q' group is, for example, phenyl or naphthyl, preferably phenyl.

A suitable value for any one of the 'Q' groups ($Q^1$, $Q^3$, $Q^5$ or $Q^6$) when it is (3–7C)cycloalkyl or for the (3–7C) cycloalkyl group within a 'Q' group is, for example, cyclopropyl, cyclobutyl, cyclopentyl, cyclohexyl, cycloheptyl or bicyclo[2.2.1]heptyl and a suitable value for any one of the 'Q' groups ($Q^1$, $Q^3$ or $Q^6$) when it is (3–7C)cycloalkenyl or for the (3–7C)cycloalkenyl group within a 'Q' group is, for example, cyclobutenyl, cyclopentenyl, cyclohexenyl or cycloheptenyl.

A suitable value for any one of the 'Q' groups ($Q^1$ to $Q^7$) when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

A suitable value for any one of the 'Q' groups ($Q^1$ to $Q^7$) when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, oxepanyl, tetrahydrothienyl, 1,1-dioxotetrahydrothienyl, tetrahydrothiopyranyl, 1,1-dioxotetrahydrothiopyranyl, azetidinyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, preferably tetrahydrofuranyl, tetrahydropyranyl, pyrrolidinyl, morpholinyl, 1,1-dioxotetrahydro-4H-1,4-thiazinyl, piperidinyl or piperazinyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for a 'Q' group when it is heteroaryl-(1–6C)alkyl is, for example, heteroarylmethyl, 2-heteroarylethyl and 3-heteroarylpropyl. The invention comprises corresponding suitable values for 'Q' groups when, for example, rather than a heteroaryl-(1–6C)alkyl group, an aryl-(1–6C)alkyl, (3–7C)cycloalkyl-(1–6C)alkyl, (3–7C)cycloalkenyl-(1–6C)alkyl or heterocyclyl-(1–6C)alkyl group is present.

In structural Formula I there is a hydrogen atom at the 2-position on the quinoline ring. It is to be understood thereby that the $R^1$ substituents may only be located at the 5-, 6-, 7- or 8-positions on the quinoline ring i.e. that the 2-position remains unsubstituted. It is further to be understood that the $R^3$ group that may be present on the benzofuranyl group within structural Formula I may be located on either the 5- or 6-membered ring portions thereof, for example at the 2-, 3-, 4-, 5- or 6-positions of the benzofuran-7-yl group. It is to be further understood that, when multiple $R^3$ groups are present, the $R^5$ groups may be the same or different. It is further to be understood that the -$Z^2$-$R^{14}$ group within structural Formula I may only be located on the 6 membered ring within the benzofuran-7-yl group.

For the avoidance of doubt, the positions on structural Formula I are numbered as follows:

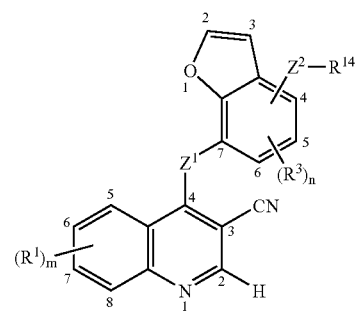

Suitable values for any of the 'R' groups ($R^1$ to $R^{19}$) or for various groups within an $R^1$, $R^3$ or $R^{14}$ group include:
for halogeno fluoro, chloro, bromo and iodo;
for (1–6C)alkyl: methyl, ethyl, propyl, isopropyl and tert-butyl;
for (2–8C)alkenyl: vinyl, isopropenyl, allyl and but-2-enyl;
for (2–8C)alkynyl: ethynyl, 2-propynyl and but-2-ynyl;
for (1–6C)alkoxy: methoxy, ethoxy, propoxy, isopropoxy and butoxy;
for (2–6C)alkenyloxy: vinyloxy and allyloxy;
for (2–6C)alkynyloxy: ethynyloxy and 2-propynyloxy;
for (1–6C)alkylthio: methylthio, ethylthio and propylthio;
for (1–6C)alkylsulphinyl: methylsulphinyl and ethylsulphinyl;
for (1–6C)alkylsulphonyl: methylsulphonyl and ethylsulphonyl;
for (1–6C)alkylamino: methylamino, ethylamino, propylamino, isopropylamino and butylamino;
for di-[(1–6C)alkyl]amino: dimethylamino, diethylamino, N-ethyl-N-methylamino and diisopropylamino;
for (1–6C)alkoxycarbonyl: methoxycarbonyl, ethoxycarbonyl, propoxycarbonyl and tert-butoxycarbonyl;
for N-(1–6C)alkylcarbamoyl: N-methylcarbamoyl, N-ethylcarbamoyl and N-propylcarbamoyl;
for N,N-di-[(1–6C)alkyl]carbamoyl: N,N-dimethylcarbamoyl, N-ethyl-N-methylcarbamoyl and N,N-diethylcarbamoyl;
for (2–6C)alkanoyl: acetyl and propionyl;
for (2–6C)alkanoyloxy: acetoxy and propionyloxy;
for (2–6C)alkanoylamino: acetamido and propionamido;
for N-(1–6C)alkyl-(2–6C)alkanoylamino: N-methylacetamido and N-methylpropionamido;
for N-(1–6C)alkylsulphamoyl: N-methylsulphamoyl and N-ethylsulphamoyl;
for N,N-di-[(1–6C)alkyl]sulphamoyl: N,N-dimethylsulphamoyl;
for (1–6C)alkanesulphonylamino: methanesulphonylamino and ethanesulphonylamino;

for N-(1–6C)alkyl-(1–6C)alkanesulphonylamino: N-methylmethanesulphonylamino and N-methylethanesulphonylamino;

for (3–6C)alkenoylamino: acrylamido, methacrylamido and crotonamido;

for N-(1–6C)alkyl-(3–6C)alkenoylamino: N-methylacrylamido and N-methylcrotonamido;

for (3–6C)alkynoylamino: propiolamido;

for N-(1–6C)alkyl-(3–6C)alkynoylamino: N-methylpropiolamido;

for amino-(1–6C)alkyl: aminomethyl, 2-aminoethyl, 1-aminoethyl and 3-aminopropyl;

for (1–6C)alkylamino-(1–6C)alkyl: methylaminomethyl, ethylaminomethyl, 1-methylaminoethyl, 2-methylaminoethyl, 2-ethylaminoethyl and 3-methylaminopropyl;

for di-[(1–6C)alkyl]amino-(1–6C)alkyl: dimethylaminomethyl, diethylaminomethyl, 1-dimethylaminoethyl, 2-dimethylaminoethyl and 3-dimethylaminopropyl;

for halogeno-(1–6C)alkyl: chloromethyl, 2-chloroethyl, 1-chloroethyl and 3-chloropropyl;

for hydroxy-(1–6C)alkyl: hydroxymethyl, 2-hydroxyethyl, 1-hydroxyethyl and 3-hydroxypropyl;

for (1–6C)alkoxy-(1–6C)alkyl: methoxymethyl ethoxymethyl, 1-methoxyethyl, 2-methoxyethyl, 2-ethoxyethyl and 3-methoxypropyl;

for cyano-(1–6C)alkyl: cyanomethyl, 2-cyanoethyl, 1-cyanoethyl and 3-cyanopropyl;

for (2–6C)alkanoylamino-(1–6C)alkyl: acetamidomethyl, propionamidomethyl and 2-acetamidoethyl; and for (1–6C)alkoxycarbonylamino-(1–6C)alkyl: methoxycarbonylaminomethyl, ethoxycarbonylaminomethyl, tert-butoxycarbonylaminomethyl and 2-methoxycarbonylaminoethyl.

A suitable value for $(R^1)_m$ when it is a (1–3C)alkylenedioxy group is, for example, methylenedioxy or ethylenedioxy and the oxygen atoms thereof occupy adjacent ring positions.

When, as defined hereinbefore, an $R^1$ group forms a group of the formula $Q^1$-$X^1$— and, for example, $X^1$ is a $OC(R^4)_2$ linking group, it is the carbon atom, not the oxygen atom, of the $OC(R^4)_2$ linking group which is attached to the quinoline ring and the oxygen atom is attached to the $Q^1$ group. Similarly, when, for example a $CH_3$ group within a $R^1$ substituent bears a group of the formula —$X^3$-$Q^3$ and, for example, $X^3$ is a $C(R^7)_2O$ linking group, it is the carbon atom, not the oxygen atom, of the $C(R^7)_2O$ linking group which is attached to the $CH_3$ group and the oxygen atom is linked to the $Q^3$ group. A similar convention applies to the attachment of the groups of the formulae $Q^3$-$X^3$—, and —$X^8$-$Q^6$.

As defined hereinbefore, adjacent carbon atoms in any (2–6C)alkylene chain within a $R^1$ substituent may be optionally separated by the insertion into the chain of a group such as O, CON($R^5$) or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetamido)ethoxy group.

When, as defined hereinbefore, any CH, $CH_2$ or $CH_3$ group within a $R^1$ or $R^{14}$ substituent optionally bears on each said CH, $CH_2$ or $CH_3$ group a substituent as defined hereinbefore, suitable $R^1$ or $R^{14}$ substituents so formed include, for example, hydroxy-substituted heterocyclyl-(1–6C) alkoxy groups such as 2-hydroxy-3-piperidinopropoxy and 2-hydroxy-3-morpholinopropoxy.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, quinoline derivatives of the Formula I, or pharmaceutically-acceptable salts thereof, wherein, unless otherwise stated, each of $Z^1$, m, $R^1$, n, $R^3$, $Z^2$ and $R^{14}$ has any of the meanings defined hereinbefore or in paragraphs (a) to (u) hereinafter:

(a) $Z^1$ is O, S, SO, $SO_2$, $CH_2$ or NH;

(b) $Z^1$ is O;

(c) $Z^1$ is NH;

(d) $R^1$ substituents may only be located at the 5-, 6- and/or 7-positions on the quinoline ring i.e. the 2- and 8-positions remain unsubstituted;

(e) $R^1$ substituents may only be located at the 6- and/or 7-positions on the quinoline ring i.e. the 2-, 5- and 8-positions remain unsubstituted;

(f) m is 1 or 2, and each $R^1$ group, which may be the same or different, is selected from halogeno, trifluoromethyl, hydroxy, amino, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino and N-(1–6C)alkyl-(3–6C)alkynoylamino or from a group of the formula:

$Q^1$-$X^1$— wherein $X^1$ is a direct bond or is selected from O, N($R^4$), CON($R^4$), N($R^4$)CO and OC($R^4$)$_2$ wherein $R^4$ is hydrogen or (1–6C)alkyl, and $Q^1$ is aryl, aryl-(1–6C)alkyl, cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within a $R^1$ substituent are optionally separated by the insertion into the chain of a group selected from O, N($R^5$), CON($R^5$), N($R^5$)CO, CH═CH and C≡C wherein $R^5$ is hydrogen or (1–6C)alkyl, or, when the inserted group is N($R^5$), $R^5$ may also be (2–6C)alkanoyl, and wherein any $CH_2$═CH— or HC≡C— group within a $R^1$ substituent optionally bears at the terminal $CH_2$═ or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^2$-$X^2$— wherein $X^2$ is a direct bond or is CO or N($R^6$)CO, wherein $R^6$ is hydrogen or (1–6C)alkyl, and $Q^2$ is heteroaryl, heteroaryl-(1–6C)alkyl, heterocyclyl or heterocyclyl-(1–6C) alkyl, and wherein any $CH_2$ or $CH_3$ group within a $R^1$ substituent optionally bears on each said $CH_2$ or $CH_3$ group one or more halogeno groups or a substituent selected from hydroxy, amino, (1–6C)alkoxy, (1–6C)alkylsulphonyl, (1–6C)alkylamino, di-[(1–6C)alkyl]amino, (2–6C)alkanoyloxy, (2–6C)alkanoylamino, N-(1–6C)alkyl-(2–6C)alkanoylamino or from a group of the formula:

—$X^3$-$Q^3$ wherein $X^3$ is a direct bond or is selected from O, N($R^6$), CON($R^7$), N($R^7$)CO and C($R^7$)$_2$O, wherein $R^7$ is hydrogen or (1–6C)alkyl, and $Q^3$ is heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1–6C)alkyl, (2–8C)alkenyl, (2–8C)alkynyl, (1–6C)alkoxy, (1–6C)alkylsulphonyl, N-(1–6C)alkylcarbamoyl, N,N-di-[(1–6C)alkyl]carbamoyl and (2–6C)alkanoyl, or optionally bears 1 substituent selected from a group of the formula:

—$X^4$—$R^8$ wherein $X^4$ is a direct bond or is selected from O and N($R^9$), wherein $R^9$ is hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl or from a group of the formula:

—$X^5$-$Q^4$ wherein $X^5$ is a direct bond or is selected from O, N($R^{10}$) and CO, wherein $R^{10}$ is hydrogen or (1–6C)alkyl, and $Q^4$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo substituents;

(g) m is 1 or 2, and each $R^1$ group, which may be the same or different, is selected from fluoro, chloro, trifluoromethyl, hydroxy, amino, carbamoyl, methyl, ethyl, propyl, butyl, vinyl, allyl, but-3-enyl, pent-4-enyl, hex-5-enyl, ethynyl, 2-propynyl, but-3-ynyl, pent-4-ynyl, hex-5-ynyl, methoxy, ethoxy, propoxy, isopropoxy, butoxy, allyloxy, but-3-enyloxy, pent-4-enyloxy, hex-5-enyloxy, ethynyloxy, 2-propynyloxy, but-3-ynyloxy, pent-4-ynyloxy, hex-5-ynyloxy, methylamino, ethylamino, propylamino, dimethylamino, diethylamino, dipropylamino, N-methylcarbamoyl, N,N-dimethylcarbamoyl, acetamido, propionamido, acrylamido and propiolamido or from a group of the formula:

$Q^1$-$X^1$— wherein $X^1$ is a direct bond or is selected from O, NF, CONH, NHCO and OCH$_2$ and $Q^1$ is phenyl, benzyl, cyclopropylmethyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-(2-, 3- or 4-pyridyl)ethyl, 3-(2-, 3- or 4-pyridyl)propyl, tetrahydrofuran-3-yl, 3- or 4-tetrahydropyranyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2–6C)alkylene chain within a $R^1$ substituent are optionally separated by the insertion into the chain of a group selected from O, NH, N(Me), CONK, NHCO, CH=CH and C≡C, and wherein any CH$_2$=CH— or HC≡C— group within a $R^1$ substituent optionally bears at the terminal CH$_2$= or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, 3-aminopropyl, 4-aminobutyl, methylaminomethyl, 2-methylaminoethyl, 3-methylaminopropyl, 4-methylaminobutyl, dimethylaminomethyl, 2-dimethylaminoethyl, 3-dimethylaminopropyl or 4-dimethylaminobutyl, or from a group of the formula:

$Q^2$-$X^2$— wherein $X^2$ is a direct bond or is CO, NHCO or N(Me)CO and $Q^2$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any CH$_2$ or CH$_3$ group within a $R^1$ substituent optionally bears on each said CH$_2$ or CH$_3$ group one or more fluoro or chloro groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido or from a group of the formula:

—$X^3$-$Q^3$ wherein $X^3$ is a direct bond or is selected from O, NH, CONH, NHCO and CH$_2$O and $Q^3$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-1-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl, allyl, 2-propynyl, methoxy, methylsulphonyl, N-methylcarbamoyl, N,N-dimethylcarbamoyl and acetyl or optionally bears 1 substituent selected from a group of the formula:

—X$^4$—R$^8$ wherein X$^4$ is a direct bond or is selected from O and NH and R$^8$ is 2-fluoroethyl, 3-fluoropropyl, 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl, tert-butoxycarbonylaminomethyl or a group of the formula:

—X$^5$-Q$^4$ wherein X$^5$ is a direct bond or is selected from O, NH and CO and Q$^4$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on R$^1$ optionally bears 1 or 2 oxo substituents;

(h) m is 1 or 2, and each R$^1$ group, which may be the same or different, is selected from halogeno, trifluoromethyl, hydroxy, amino, carbamoyl, (1–6C)alkyl, (1–6C)alkoxy, (1–6C)alkylamino, di-[(1–6C)alkyl]amino, N-(1–6C)alkylcarbamoyl, N-N-di-[(1–6C)alkyl]carbamoyl, (2–6C)alkanoylamino, N-(1–6C)alkyl-(2–6C)alkanoylamino or from a group of the formula:

Q$^1$-X$^1$— wherein X$^1$ is selected from O, N(R$^4$), CON(R$^4$), N(R$^4$)CO and OC(R$^4$)$_2$ wherein R$^4$ is hydrogen or (1–6C)alkyl, and Q$^1$ is aryl, aryl-(1–6C)alkyl, cycloalkyl-(1–6C)alkyl, heteroaryl, heteroaryl-(1–6C)alkyl, heterocyclyl or heterocyclyl-(1–6C)alkyl, or X$^1$ is a direct bond and Q$^1$ is aryl-(1–6C)alkyl, cycloalkyl-(1–6C)alkyl, heteroaryl-(1–6C)alkyl or heterocyclyl-(1–6C)alkyl, and wherein adjacent carbon atoms in any (2–6C)alkylene chain within a R$^1$ substituent are optionally separated by the insertion into the chain of a group selected from O, N(R$^5$), CON(R$^5$), N(R$^5$)CO, CH=CH and C≡C wherein R$^5$ is hydrogen or (1–6C)alkyl, or, when the inserted group is N(R$^5$), R$^5$ may also be (2–6C)alkanoyl, and wherein any CH$_2$ or CH$_3$ group within a R$^1$ substituent optionally bears on each said CH$_2$ or CH$_3$ group one or more halogeno groups or a substituent selected from hydroxy, amino, (1–6C)alkoxy, (1–6C)alkylsulphonyl, (1–6C)alkylamino, di-[(1–6C)alkyl]amino, (2–6C)alkanoyloxy, (2–6C)alkanoylamino, N-(1–6C)alkyl-(2–6C)alkanoylamino or a group of the formula:

—X$^3$-Q$^3$ wherein X$^3$ is a direct bond or is selected from O, N(R$^6$), CON(R$^7$), N(R$^7$)CO and C(R$^7$)$_2$O, wherein R$^7$ is hydrogen or (1–6C)alkyl, and Q$^3$ is heteroaryl, heteroaryl-(1–6C)alkyl, heterocyclyl or heterocyclyl (1–6C)alkyl, and wherein any aryl, heteroaryl or heterocyclyl group within a substituent on R$^1$ optionally bears 1, 2 or 3 substituents, which may be the same or different, selected from halogeno, trifluoromethyl, hydroxy, amino, carbamoyl, (1–6C)alkyl, (2–8C)alkenyl, (2–8C)alkynyl, (1–6C)alkoxy, (1–6C)alkylsulphonyl, N-(1–6C)alkylcarbamoyl, N,N-di-[(1–6C)alkyl]carbamoyl and (2–6C)alkanoyl, or optionally bears 1 substituent selected from a group of the formula:

—X$^4$—R$^8$ wherein X$^4$ is a direct bond or is selected from O and N(R$^9$), wherein R$^9$ is hydrogen or (1–6C)alkyl, and R$^8$ is hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl or from a group of the formula:

—X$^5$-Q$^4$ wherein X$^5$ is a direct bond or is selected from O, N(R$^{10}$) and CO, wherein R$^{10}$ is hydrogen or (1–6C)alkyl, and Q$^4$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on R$^1$ optionally bears 1 or 2 oxo substituents;

(i) m is 1 or 2, and each R$^1$ group, which may be the same or different, is selected from fluoro, chloro, trifluoromethyl, hydroxy, amino, carbamoyl, methyl, ethyl, propyl, butyl, methoxy, ethoxy, propoxy, isopropoxy, butoxy, methylamino, ethylamino, propylamino, dimethylamino, diethylamino, dipropylamino, N-methylcarbamoyl, N,N-dimethylcarbamoyl, acetamido, propionamido, acrylamido, propiolamido or from a group of the formula:

Q$^1$-X$^1$— wherein X$^1$ is selected from O, NH, CONH, NHCO and OCH$_2$ and Q$^1$ is phenyl, benzyl, cyclopropylmethyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-(2-, 3- or 4-pyridyl)ethyl, 3-(2-, 3- or 4-pyridyl)propyl, tetrahydrofuran-3-yl, 3- or 4-tetrahydropyranyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, or wherein X$^1$ is a direct bond and Q$^1$ is benzyl, cyclopropylmethyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-2-,3- or 4-pyridyl)ethyl, 3-(2-, 3- or 4-pyridyl)propyl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein adjacent carbon atoms in any (2–6C)alkylene chain within a $R^1$ substituent are optionally separated by the insertion into the chain of a group selected from O, NH, N(Me), CONH, NHCO, CH=CH and C≡C, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido, N-methylacetamido or from a group of the formula:

—$X^3$-$Q^3$ wherein $X^3$ is a direct bond or is selected from O, NH, CONH, NHCO and $CH_2O$ and $Q^3$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

—$X^4$—$R^8$ wherein $X^4$ is a direct bond or is selected from O and NH and $R^8$ is 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl, tert-butoxycarbonylaminomethyl or from a group of the formula:

—$X^5$-$Q^4$ wherein $X^5$ is a direct bond or is selected from O, NH and CO and $Q^4$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(j) m is 2 and each $R^1$ group, which may be the same or different, is located at the 5- and 7-positions or at the 6- and 7-positions and $R^1$ is selected from hydroxy, amino, methyl, ethyl, propyl, methoxy, ethoxy, propoxy, isopropoxy, butoxy, pentyloxy, methylamino, ethylamino, dimethylamino, diethylamino, acetamido, propionamido, cyclopentyloxy, cyclohexyloxy, phenoxy, benzyloxy, tetrahydrofuran-3-yloxy, tetrahydropyran-3-yloxy, tetrahydropyran-4-yloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, pyrid-2-ylmethoxy, pyrid-3-ylmethoxy, pyrid-4-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy, 3-homopiperazin-1-ylpropoxy, 2-pyrrolidin-1-ylethylamino, 3-pyrrolidin-1-ylpropylamino, 4-pyrrolidin-1-ylbutylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 4-morpholinobutylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, 4-piperidinobutylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 4-piperazin-1-ylbutylamino, 2-homopiperazin-1-ylethylamino or 3-homopiperazin-1-ylpropylamino, and wherein adjacent carbon atoms in any (2–6C)alkylene chain within a $R^1$ substituent are optionally separated by the insertion into the chain of a group selected from O, NH, N(Me), CH=CH and C≡C, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido, and wherein any phenyl, imidazolyl, triazolyl, pyridyl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, N-methylcarbamoyl, N-N-dimethylcarbamoyl and methoxy, and a pyrrolidin-2-yl, piperidin-3-yl, piperidin-4-yl, piperazin-1-yl or homopiperazin-1-yl group within a $R^1$ substituent is optionally N-substituted with allyl, 2-propynyl, methylsulphonyl, acetyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;
(k) n is 0;
(l) n is 1 or 2 and the $R^3$ groups, which may be the same or different, are located at the 5- and/or 6-positions of the benzofuran-7-yl group and are selected from halogeno, trifluoromethyl, cyano, hydroxy, (1–6C)alkyl, (2–8C)alkenyl, (2–8C)alkynyl, (1–6C)alkoxy, (1–6C)alkylthio, (1–6C)alkylsulphinyl, (1–6C)alkylsulphonyl or from a group of the formula:

$$—X^6—R^{11}$$

wherein $X^6$ is a direct bond and $R^{11}$ is hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(–6C)alkyl;
(m) n is 1 or 2 and the $R^3$ groups, which may be the same or different, are located at the 5- and/or 6-positions of the benzofuran-7-yl group and are selected from halogeno, trifluoromethyl, cyano, hydroxy, (1–6C)alkyl, (2–8C)alkenyl, (2–8C)alkynyl and (1–6C)alkoxy;
(n) n is 1 or 2 and the $R^3$ groups, which may be the same or different, are located at the 5- and/or 6-positions of the benzofuran-7-yl group and are selected from fluoro, chloro, bromo, iodo, trifluoromethyl, cyano, hydroxy, methyl, ethyl, vinyl, allyl, isopropenyl, ethynyl, 1-propynyl, 2-propynyl, methoxy and ethoxy;
(o) n is 1 and the $R^3$ group is located at the 5- or 6-position of the benzofuran-7-yl group group and is selected from chloro, bromo, trifluoromethyl, cyano, hydroxy, methyl, ethyl, methoxy and ethoxy;
(p) the $-Z^2-R^{14}$ group is located at the 4-position on the benzofuran-7-yl group;
(q) $Z^2$ is a C≡C group;
(r) $Z^2$ is a CH=CH group;
(s) $R^{14}$ is selected from halogeno, cyano, formyl, carboxy, carbamoyl, (1–6C)alkoxycarbonyl, N-(1–6C)alkylcarbamoyl, N,N-di-[(1–6C)alkyl]carbamoyl, (2–6C)alkanoyl, N-(1–6C)alkylsulphamoyl, N,N-di-[(1–6C)alkyl]sulphamoyl, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or from a group of the formula:

$$—X^7-Q^5$$

wherein $X^7$ is a direct bond or CO and $Q^5$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a $R^{14}$ substituent optionally bears on each said $CH_2$ or $CH_3$ group one or more halogeno or (1–6C)alkyl substituents or a substituent selected from hydroxy, cyano, amino, (1–6C)alkoxy, (1–6C)alkylthio, (1–6C)alkylsulphinyl, (1–6C)alkylsulphonyl, (1–6C)alkylamino, di-[(1–6C)alkyl]amino, (2–6C)alkanoyl, (2–6C)alkanoyloxy, (2–6C)alkanoylamino, N-(1–6C)alkyl-(2–6C)alkanoylamino or from a group of the formula:

$$—X^8-Q^6$$

wherein $X^8$ is a direct bond or is selected from O, N($R^{16}$), CON($R^{16}$), N($R^{16}$)CO and C($R^{16}$)$_2$O, wherein $R^{16}$ is hydrogen or (1–6C)alkyl, and $Q^6$ is heteroaryl, heteroaryl-(1–6C)alkyl, heterocyclyl or heterocyclyl-(1–6C)alkyl, and wherein any aryl, heteroaryl or heterocyclyl group within a substituent on $R^{14}$ optionally bears 1, 2 or 3 substituents, which may be the same or different, selected from halogeno, trifluoromethyl, hydroxy, amino, carbamoyl, (1–6C)alkyl, (2–8C)alkenyl, (2–8C)alkynyl, (1–6C)alkoxy, (1–6C)alkylsulphonyl, N-(1–6C)alkylcarbamoyl, N,N-di-[(1–6C)alkyl]carbamoyl and (2–6C)alkanoyl, or optionally bears 1 substituent selected from a group of the formula:

$$—X^9—R^{17}$$

wherein $X^9$ is a direct bond or is selected from O and N($R^{18}$), wherein $R^{18}$ is hydrogen or (1–6C)alkyl, and $R^{17}$ is hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl, and from a group of the formula:

$$—X^{10}-Q^7$$

wherein $X^{10}$ is a direct bond or is selected from O, N($R^{19}$) and CO, wherein $R^{19}$ is hydrogen or (1–6C)alkyl, and $Q^7$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^{14}$ optionally bears 1 or 2 oxo substituents;
(t) $R^{14}$ is selected from chloro, cyano, formyl, carboxy, carbamoyl, methoxycarbonyl, ethoxycarbonyl, N-methylcarbamoyl, N-ethylcarbamoyl, N,N-dimethylcarbamoyl, N-ethyl-N-methylcarbamoyl, N,N-diethylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, cyanomethyl, 2-cyanoethyl, 3-cyanopropyl, aminomethyl, 2-aminoethyl, 3-aminopropyl, methylaminomethyl, ethylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, 2-acetamidoethyl, 3-acetamidopropyl or from a group of the formula:

$$—X^7-Q^5$$

wherein $X^7$ is a direct bond or CO and $Q^5$ is phenyl, benzyl, 1-, 2- or 3-pyrrolidinyl, morpholino, 1,1-dioxotetrahydro-1H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 1,1-dioxotetrahydro-4H-1,4-thiazin-4-ylmethyl, piperazin-1-ylmethyl, homopiperazin-1-ylmethyl, 2-pyrrolidin-1-ylethyl, 3-pyrrolidin-1-ylpropyl, 2-pyrrolidin-2-ylethyl, 3-pyrrolidin-2-ylpropyl, 2-morpholinoethyl, 3-morpholinopropyl, 2-(1,1-dioxotetrahydro-4H-1, 4-thiazin-4-yl)ethyl, 3-(1,1-dioxotetrahydro-4H-1,4-thiazin-4-yl)propyl, 2-piperidinoethyl 3-piperidinopropyl, 2-piperidin-3-ylethyl, 3-piperidin-3-ylpropyl, 2-piperidin-4-ylethyl 3-piperidin-4-ylpropyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein any $CH_2$ or $CH_3$ group within a $R^{14}$ substituent optionally bears on each said $CH_2$ or $CH_3$ group one or more fluoro, chloro or methyl groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetoxy, acetamido and N-methylacetamido, or from a group of the formula:

$$-X^1-Q^6$$

wherein $X^8$ is a direct bond or is selected from O, NH, CONH, NHCO and $CH_2O$ and $Q^6$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^{14}$ optionally bears 1, 2 or 3 substituents, which may be the same or different, selected from fluoro, chloro, trifluoromethyl, hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

$$-X^9-R^{17}$$

wherein $X^9$ is a direct bond or is selected from O and NH and $R^{17}$ is 2-fluoroethyl, 3-fluoropropyl, 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl, tert-butoxycarbonylaminomethyl and from a group of the formula:

$$-X^{10}-Q^7$$

wherein $X^{10}$ is a direct bond or is selected from O, NH and CO and $Q^7$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^{14}$ optionally bears 1 or 2 oxo substituents; and (u) $R^{14}$ is selected from cyano, formyl, carboxy, carbamoyl, methoxycarbonyl, ethoxycarbonyl, N-methylcarbamoyl, N-ethylcarbamoyl, N,N-dimethylcarbamoyl, N-ethyl-N-methylcarbamoyl, N,N-diethylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl or from a group of the formula:

$$-X^7-Q^5$$

wherein $X^7$ is a direct bond or CO and $Q^5$ is 1-pyrrolidinyl, morpholino, 1,1-dioxotetrahydro-4H-1,4-thiazin-4-yl, piperidino, 1-homopiperidinyl, piperazin-1-yl, homopiperazin-1-yl, 1-pyrrolidinylmethyl, morpholinomethyl, piperidinomethyl, 1-homopiperidinylmethyl, 1,1-dioxotetrahydro-4H-1,4-thiazin-4-ylmethyl, piperazin-1-ylmethyl, homopiperazin-1-ylmethyl or 3-morpholinopropyl, and wherein any $CH_2$ or $CH_3$ group within a $R^{14}$ substituent optionally bears on each said $CH_2$ or $CH_3$ group one or more fluoro, chloro or methyl groups or a substituent selected from hydroxy, amino, methoxy, methylamino, dimethylamino, acetoxy, acetamido and N-methylacetamido, and wherein any heterocyclyl group within a substituent on $R^{14}$ optionally bears 1, 2 or 3 substituents, which may be the same or different, selected from hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

$$-X^9-R^{17}$$

wherein $X^9$ is a direct bond and $R^{17}$ is 2-fluoroethyl, 2-hydroxyethyl, 3-hydroxypropyl, 2-methoxyethyl, 3-methoxypropyl, cyanomethyl, aminomethyl, methylaminomethyl, dimethylaminomethyl, acetamidomethyl, methoxycarbonylaminomethyl, ethoxycarbonylaminomethyl or tert-butoxycarbonylaminomethyl, and wherein any heterocyclyl group within a substituent on $R^{14}$ optionally bears 1 or 2 oxo substituents.

A particular compound of the invention is a quinoline derivative of the Formula I wherein:

$Z^1$ is O or NH;

m is 1 and the $R^1$ group is located at the 5-, 6- or 7-position or m is 2 and each $R^1$ group, which may be the same or different, is located at the 5- and 7-positions or at the 6- and 7-positions and $R^1$ is selected from hydroxy, amino, methyl, ethyl, propyl, butyl, methoxy, ethoxy, propoxy, isopropoxy, butoxy, pent-4-ynyloxy, hex-5-ynyloxy, methylamino, ethylamino, dimethylamino, diethylamino, acetamido, propionamido, 2-imidazol-1-ylethoxy, 2-(1,2,4-triazol-1-yl)ethoxy, tetrahydrofuran-3-yloxy, tetrahydropyran-4-yloxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy and 3-homopiperazin-1-ylpropoxy, and wherein adjacent carbon atoms in any (2–6C)alkylene chain within a $R^1$ substituent are optionally separated by the insertion into the chain of a group selected from O, NH, N(Me), CH=CH and C≡C, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methylamino, dimethylamino, diethylamino, N-ethyl-N-methylamino, N-isopropyl-N-methylamino, N-methyl-N-propylamino and acetoxy;

and wherein any heteroaryl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, N-methylcarbamoyl and N,N-dimethylcarbamoyl and a pyrrolidin-2-yl, piperidin-3-yl, piperidin-4-yl, piperazin-1-yl or homopiperazin-1-yl group within a $R^1$ substituent is optionally N-substituted with allyl, methylsulphonyl, acetyl, 2-fluoroethyl, 3-fluoropropyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

n is 0 or 1 and the $R^3$ group, if present, is located at the 5- or 6-position of the benzofuran-7-yl group and is selected from fluoro, chloro, bromo, trifluoromethyl, cyano, hydroxy, methyl, ethyl, vinyl, allyl, ethynyl, methoxy and ethoxy;

$Z^2$ is a C≡C or CH=CH group; and $R^{14}$ is selected from cyano, formyl, carboxy, carbamoyl, methoxycarbonyl, ethoxycarbonyl, N-methylcarbamoyl, N-ethylcarbamoyl, N,N-dimethylcarbamoyl, N-ethyl-N-methylcarbamoyl, N,N-diethylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, cyanomethyl, 2-cyanoethyl, 3-cyanopropyl, methylaminomethyl, ethylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, 2-acetamidoethyl and 3-acetamidopropyl, or from a group of the formula:

$$-X^7-Q^5$$

wherein $X^7$ is a direct bond or CO and $Q^5$ is 1-pyrrolidinyl, morpholino, 1,1-dioxotetrahydro-4H-1,4-thiazin-4-yl, piperidino, 1-homopiperidinyl, piperazin-1-yl, homopiperazin-1-yl, 1-pyrrolidinylmethyl, morpholinomethyl, piperidinomethyl, 1-homopiperidinylmethyl, 1,1-dioxotetrahydro-4H-1,4-thiazin-4-ylmethyl, piperazin-1-ylmethyl, homopiperazin-1-ylmethyl or 3-morpholinopropyl, and wherein any $CH_2$ or $CH_3$ group within a $R^{14}$ substituent optionally bears on each said $CH_2$ or $CH_3$ group one or more fluoro, chloro or methyl groups or a substituent selected from hydroxy, amino, methoxy, methylamino, dimethylamino, acetoxy, acetamido and N-methylacetamido, and wherein any heterocyclyl group within a substituent on $R^{14}$ optionally bears 1, 2 or 3 substituents, which may be the same or different, selected from hydroxy, amino, carbamoyl, methyl, ethyl, allyl, 2-propynyl, methoxy, methylsulphonyl, N-methylcarbamoyl, N,N-dimethylcarbamoyl and acetyl, or optionally bears 1 substituent selected from a group of the formula:

$$-X^9-R^{17}$$

wherein $X^9$ is a direct bond and $R^{17}$ is 2-hydroxyethyl, 3-hydroxypropyl, 2-methoxyethyl, 3-methoxypropyl, cyanomethyl, aminomethyl, methylaminomethyl, dimethylaminomethyl, acetamidomethyl, methoxycarbonylaminomethyl, ethoxycarbonylaminomethyl or tert-butoxycarbonylaminomethyl, and wherein any heterocyclyl group within a substituent on $R^{14}$ optionally bears 1 or 2 oxo substituents;

or a pharmaceutically-acceptable acid-addition salt thereof

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-methylsulphonylethoxy, 3-methylsulphonylpropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3–1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy, 2-(2-pyrrolidin-1-ylethoxy)ethoxy, 2-(2-morpholinoethoxy)ethoxy, 2-(2-piperidinoethoxy)ethoxy and 2-[2-(4-methylpiperazin-1-yl)ethoxy]ethoxy;

n is 0 or n is 1 and the $R^3$ group, if present, is located at the 5-position of the benzofuran-7-yl group and is selected from chloro and bromo;

the -$Z^2$-$R^{14}$ group is located at the 4-position on the benzofuran-7-yl group, $Z^2$ is a C≡C or CH=CH group; and $R^{14}$ is selected from cyano, formyl, carboxy, carbamoyl, methoxycarbonyl, ethoxycarbonyl, N-methylcarbamoyl, N-ethylcarbamoyl, N-(2-methoxyethyl)carbamoyl, N,N-dimethylcarbamoyl, N-ethyl-N-methylcarbamoyl, N-(2-methoxyethyl)-N-methylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, dimethylaminomethyl, 2-dimethylaminoethyl, 3-dimethylaminopropyl, 1-pyrrolidinylcarbonyl, morpholinocarbonyl, 1,1-dioxotetrahydro-4H-1,4-thiazin-4-ylcarbonyl, piperidinocarbonyl, piperazin-1-ylcarbonyl, 1-pyrrolidinylmethyl, morpholinomethyl, piperidinomethyl, 1,1-dioxotetrahydro-4H-1,4-thiazin-4-ylmethyl, piperazin-1-ylmethyl and 3-morpholinopropyl;

or a pharmaceutically-acceptable acid-addition salt thereof

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-methylsulphonylethoxy, 3-methylsulphonylpropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy, 2-(2-pyrrolidin-1-ylethoxy)ethoxy, 2-(2-morpholinoethoxy)ethoxy, 2-(2-piperidinoethoxy)ethoxy and 2-[2-(4-methylpiperazin-1-yl)ethoxy]ethoxy;

n is 0 or n is 1 and the $R^3$ group, if present, is located at the 5-position of the 1,3-benziodioxol-4-yl group and is selected from chloro and bromo;

the -$Z^2$-$R^{14}$ group is located at the 4-position on the benzofuran-7-yl group, $Z^2$ is a C≡C group; and $R^{14}$ is selected from chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, dimethylaminomethyl, 2-dimethylaminoethyl, 3-dimethylaminopropyl, 1-pyrrolidinylmethyl, morpholinomethyl, piperidinomethyl, 1,1-dioxotetrahydro-4H-1,4-thiazin-4-ylmethyl, piperazin-1-ylmethyl and 3-morpholinopropyl;

or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-methylsulphonylethoxy, 3-methylsulphonylpropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy, 2-(2-pyrrolidin-1-ylethoxy)ethoxy, 2-(2-morpholinoethoxy)ethoxy, 2-(2-piperidinoethoxy)ethoxy and 2-[2-(4-methylpiperazin-1-yl)ethoxy]ethoxy;

n is 0 or n is 1 and the $R^3$ group, if present, is located at the 5-position of the benzofuran-7-yl group and is selected from chloro and bromo;

the -$Z^2$-$R^{14}$ group is located at the 4-position on the benzofuran-7-yl group, $Z^2$ is a CH═CH group; and $R^{14}$ is selected from cyano, formyl, carboxy, carbamoyl, methoxycarbonyl, ethoxycarbonyl, N-methylcarbamoyl, N-ethylcarbamoyl, N-(2-methoxyethyl)carbamoyl, N,N-dimethylcarbamoyl, N-ethyl-N-methylcarbamoyl, N-(2-methoxyethyl)-N-methylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, dimethylaminomethyl, 2-dimethylaminoethyl, 3-dimethylaminopropyl, 1-pyrrolidinylcarbonyl, morpholinocarbonyl, 1,1-dioxotetrahydro-4H-1,4-thiazin-4-ylcarbonyl, piperidinocarbonyl, piperazin-1-ylcarbonyl, 1-pyrrolidinylmethyl, morpholinomethyl, piperidinomethyl, 1,1-dioxotetrahydro-4H-1,4-thiazin-4-ylmethyl and piperazin-1-ylmethyl;

or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy and 2-(2-pyrrolidin-1-ylethoxy)ethoxy;

n is 0 or n is 1 and $R^3$ is a chloro group located at the 5-position of the benzofuran-7-yl group;

the -$Z^2$-$R^{14}$ group is located at the 4-position on the benzofuran-7-yl group, $Z^2$ is a C≡C group; and $R^{14}$ is selected from hydroxymethyl, methoxymethyl, dimethylaminomethyl, 1-pyrrolidinylmethyl, morpholinomethyl, piperidinomethyl, 1,1-dioxotetrahydro-4H-1,4-thiazin-4-ylmethyl and piperazin-1-ylmethyl;

or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, and 3-(3-oxopiperazin-1-yl)propoxy;

n is 0;

the -$Z^2$-$R^{14}$ group is located at the 4-position on the benzofuran-7-yl group;

$Z^2$ is a C≡C group; and $R^{14}$ is selected from hydroxymethyl and methoxymethyl or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, 2-(4-methylpiperazin-1-yl)ethoxy and 3-(4-methylpiperazin-1-yl)propoxy;

n is 0;

the -$Z^2$-$R^{14}$ group is located at the 4-position on the benzofuran-7-yl group, $Z^2$ is a C≡C group; and $R^{14}$ is selected from hydroxymethyl and methoxymethyl or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy and 2-(2-pyrrolidin-1-ylethoxy)ethoxy;

n is 0 or n is 1 and $R^3$ is a chloro group located at the 5-position of the 1,3-benziodioxol-4-yl group;

the -$Z^2$-$R^{14}$ group is located at the 4-position on the benzofuran-7-yl group, $Z^2$ is a CH=CH group; and $R^{14}$ is selected from cyano, carboxy, carbamoyl, methoxycarbonyl, ethoxycarbonyl, N-methylcarbamoyl, N-ethylcarbamoyl, N-(2-methoxyethyl)carbamoyl, N,N-dimethylcarbamoyl, N-ethyl-N-methylcarbamoyl, N-(2-methoxyethyl)-N-methylcarbamoyl, acetyl, propionyl, 1-pyrrolidinylcarbonyl, morpholinocarbonyl, 1,1-dioxotetrahydro-4H-1,4-thiazin-4-ylcarbonyl, piperidinocarbonyl and piperazin-1-ylcarbonyl;

or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, and 3-(3-oxopiperazin-1-yl)propoxy;

n is 0;

the -$Z^2$-$R^{14}$ group is located at the 4-position on the benzofuran-7-yl group;

$Z^2$ is a CH=CH group; and $R^{14}$ is selected from methoxycarbonyl and ethoxycarbonyl;

or a pharmaceutically-acceptable acid-addition salt thereof.

A further particular compound of the invention is a quinoline derivative of the Formula I wherein:

$Z^1$ is NH;

m is 2 and the first $R^1$ group is a 6-methoxy group and the second $R^1$ group is located at the 7-position and is selected from methoxy and ethoxy;

n is 0;

the -$Z^2$-$R^{14}$ group is located at the 4-position on the benzofuran-7-yl group;

$Z^2$ is a CH=CH group; and $R^{14}$ is selected from methoxycarbonyl and ethoxycarbonyl;

or a pharmaceutically-acceptable acid-addition salt thereof.

Particular compounds of the invention include, for example, the quinoline derivatives of the Formula I described hereinafter in the Examples.

A quinoline derivative of the Formula I, or a pharmaceutically-acceptable salt thereof, may be prepared by any process known to be applicable to the preparation of chemically-related compounds. Such processes, when used to prepare a quinoline derivative of the Formula I are provided as a further feature of the invention and are illustrated by the following representative process variants in which, unless otherwise stated, m, $R^1$, $Z^1$, n, $R^3$, $Z^2$ and $R^{14}$ have any of the meanings defined hereinbefore. Necessary starting materials may be obtained by standard procedures of organic chemistry. The preparation of such starting materials is described in conjunction with the following representative process variants and within the accompanying Examples. Alternatively necessary staring materials are obtainable by analogous procedures to those illustrated which are within the ordinary skill of an organic chemist.

(a) For the production of those compounds of the Formula I wherein $Z^1$ is an O, S or N($R^2$) group, the reaction of a quinoline of the Formula II

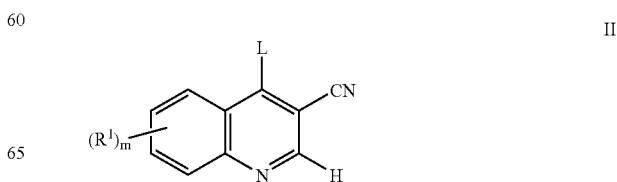

wherein L is a displaceable group and m and $R^1$ have any of the meanings defined hereinbefore except that any functional group is protected if necessary, with a compound of the Formula III

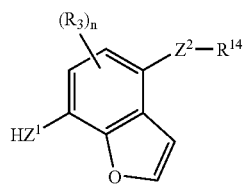

wherein $Z^1$ is O, S, or $N(R^2)$ and n, $R^3$, $R^2$, $Z^2$ and $R^{14}$ have any of the meanings defined hereinbefore except that any functional group is protected if necessary, whereafter any protecting group that is present is removed by conventional means.

The reaction may conveniently be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride.

A suitable displaceable group L is, for example, a halogeno, alkoxy, aryloxy or sulphonyloxy group, for example a chloro, bromo, methoxy, phenoxy, pentafluorophenoxy, methanesulphonyloxy or toluene-4-sulphonyloxy group. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 250° C., preferably in the range 0 to 120° C.

Typically, the quinoline of the Formula II may be reacted with a compound of the Formula III in the presence of an aprotic solvent such as N,N-dimethylformamide, conveniently in the presence of a base, for example potassium carbonate or sodium hexamethyldisilazane, and at a temperature in the range, for example, 0 to 150° C., preferably in the range, for example, 0 to 70° C.

The quinoline derivative of the Formula I may be obtained from this process in the form of the free base or alternatively it may be obtained in the form of a salt with the acid of the formula H-L wherein L has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2–6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, 2$^{nd}$ Edition, by T. Green et al., also published by John Wiley & Son, for general guidance on protecting groups.

Quinoline stating materials of the Formula II may be obtained by conventional procedures such as those disclosed in International Patent Applications WO 98/43960 and WO 00/68201. For example, a 1,4-dihydroquinolin-4-one of Formula IV

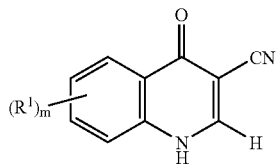

IV wherein m and R$^1$ have any of the meanings defined hereinbefore except that any functional group is protected if necessary, may be reacted with a halogenating agent such as thionyl chloride, phosphoryl chloride or a mixture of carbon tetrachloride and triphenylphosphine whereafter any protecting group that is present is removed by conventional means.

The 4-chloroquinoline so obtained may be converted, if required, into a 4-pentafluorophenoxyquinoline by reaction with pentafluorophenol in the presence of a suitable base such as potassium carbonate and in the presence of a suitable solvent such as N,N-dimethylformamide.

7-Aminobenzofuran starting materials (Formula III, for example when Z is NH) may be obtained by conventional procedures as illustrated in the Examples. Corresponding 7-hydroxybenzofuran and 7-mercaptobenzofuran starting materials (Formula III, when Z is O or S respectively) may be obtained by conventional procedures.

(b) For the production of those compounds of the Formula I wherein at least one R$^1$ group is a group of the formula $Q^1$-$X^1$— 

wherein Q$^1$ is an aryl-(1–6C)alkyl, (3–7C)cycloalkyl-(1–6C)alkyl, (3–7C)cycloalkenyl-(1–6C)alkyl, heteroaryl-(1–6C)alkyl or heterocyclyl-(1–6C)alkyl group or an optionally substituted alkyl group and X$^1$ is an oxygen atom, the coupling, conveniently in the presence of a suitable dehydrating agent, of a quinoline of the Formula V.

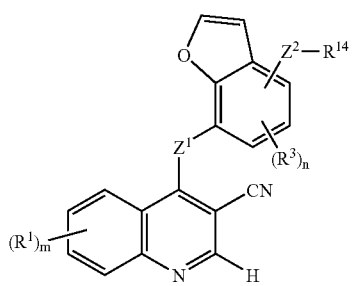

V wherein m, R$^1$, Z$^1$, n, R$^3$, Z$^2$ and R$^{14}$ have any of the meanings defined hereinbefore except that any functional group is protected if necessary, with an appropriate alcohol of the formula Q$^1$-OH wherein any functional group is protected if necessary, whereafter any protecting group that is present is removed by conventional means.

A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

(c) For the production of those compounds of the Formula I wherein R$^1$ is an amino-substituted (1–6C)alkoxy group (such as 2-homopiperidin-1-ylethoxy or 3-dimethylaminopropoxy), the reaction of a compound of the Formula I wherein R$^1$ is a halogeno-substituted (1–6C)alkoxy group with a heterocyclyl compound or an appropriate amine. The reaction is conveniently carried out in the presence of a suitable inert diluent or carrier as defined hereinbefore and at a temperature in the range 10 to 150° C., preferably at or near ambient temperature.

(d) For the production of those compounds of the Formula I wherein an R$^1$ group contains a (1–6C)alkoxy or substituted (1–6C)alkoxy group or a (1–6C)alkylamino or substituted (1–6C)alkylamino group, the alkylation, conveniently in the presence of a suitable base as defined hereinbefore, of a quinoline derivative of the Formula I wherein the R$^1$ group contains a hydroxy group or a primary or secondary amino group as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1–6C)alkyl chloride, bromide or iodide or a substituted (1–6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature.

Conveniently for the production of those compounds of the Formula I wherein R$^1$ contains a (1–6C)alkylamino or substituted (1–6C)alkylamino group, a reductive amination reaction may be employed. For example, for the production of those compounds of the Formula I wherein R$^1$ contains a N-methyl group, the corresponding compound containing a N—H group may be reacted with formaldehyde in the presence of a suitable reducing agent. A suitable reducing agent is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

(e) For the production of those compounds of the Formula I wherein $Z^1$ is a SO or $SO_2$ group, wherein an $R^1$ or $R^3$ substituent is a (1–6C)alkylsulphinyl or (1–6C)alkylsulphonyl group or wherein an $R^1$, $R^3$ or $R^{14}$ substituent contains a SO or $SO_2$ group, the oxidation of a compound of Formula I wherein $Z^1$ is a S group or wherein an $R^1$ or $R^3$ substituent is a (1–6C)alkylthio group or wherein an $R^1$, $R^3$ or $R^{14}$ substituent contains a S group as appropriate.

Conventional oxidation reagents and reaction conditions for such partial or complete oxidation of a sulphur atom are well known to the organic chemist.

(f) The reaction, conveniently in the presence of a suitable base as defined hereinbefore and in the presence of a suitable catalyst, of a compound of the Formula VI

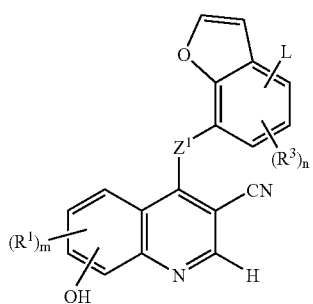

VI wherein L is a displaceable group as defined hereinbefore and m, $R^1$, $Z^1$, n and $R^3$ have any of the meanings defined hereinbefore except that any functional group is protected if necessary, with a compound of the Formula VII

HZ$^2$-R$^{14}$  VII wherein $Z^2$ is a C≡C or $C(R^{13})$=$C(R^{13})$ group and $R^{13}$ and $R^{14}$ have any of the meanings defined hereinbefore except that any functional group is protected if necessary, whereafter any protecting group that is present is removed by conventional means.

Conveniently the displaceable group is a halogeno group such as iodo, bromo or chloro. A suitable catalyst is, for example, an organometallic reagent, for example an organopalladium compound such as tetrakis(triphenylphosphine)palladium(0) or bis(triphenylphosphine)palladium(II) dichloride. The conversion reaction is conveniently carried out in the presence of a suitable inert diluent or carrier as defined hereinbefore and at a temperature in the range 10 to 150° C., preferably at or near 60° C.

(g) For the production of a compound of the Formula I wherein $R^{14}$ is a carboxy group, the cleavage of a compound of the Formula I wherein $R^{14}$ is a (1–6C)alkoxycarbonyl group.

The cleavage reaction is conveniently carried out by the hydrolysis of the (1–6C)alkoxycarbonyl group in the presence of a suitable base, for example an alkali or alkaline earth metal carbonate or hydroxide such as sodium carbonate, potassium carbonate, calcium carbonate, sodium hydroxide or potassium hydroxide and in the presence of a suitable inert diluent or carrier as defined hereinbefore such as methanol and at a temperature in the range 10 to 150° C., preferably at or near 40° C.

(h) The reaction, conveniently in the presence of a suitable dehydrating agent as defined hereinbefore, of a compound of the Formula I wherein $R^{14}$ is a carboxy group with an appropriate amine to form a further compound of the Formula I wherein $R^{14}$ is a carbamoyl, N-(1–6C)alkylcarbamoyl, N,N-di-[(1–6C)alkyl]carbamoyl or heterocyclylcarbonylamino group.

(i) a coupling reaction of a compound of the Formula VIII

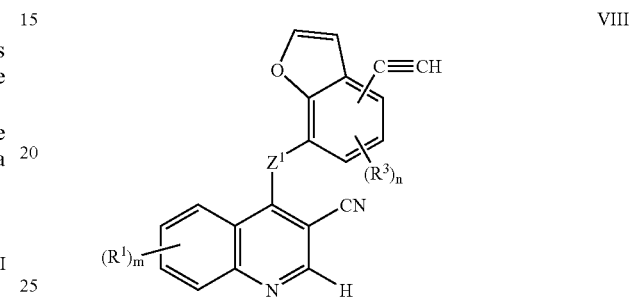

VIII wherein m, $R^1$, $Z^1$, n and $R^3$ have any of the meanings defined in claim 1 except that any functional group is protected if necessary, with a compound of the Formula IX

L-R$^{14}$  IX wherein L is a displaceable group and $R^{14}$ has any of the meanings defined in claim 1 except that any functional group is protected if necessary, whereafter any protecting group that is present is removed by conventional means;

and when a pharmaceutically-acceptable salt of a quinoline derivative of Formula I is required it may be obtained using a conventional procedure.

The reaction is conveniently carried out in the presence of a suitable inert diluent or carrier as defined hereinbefore and at a temperature in the range, for example, 10 to 150° C., preferably at or near ambient temperature.

When a pharmaceutically-acceptable salt of a quinoline derivative of the Formula I is required, for example an acid-addition salt, it may be obtained by, for example, reaction of said quinoline derivative with a suitable acid using a conventional procedure.

Biological Assays

The following assays can be used to measure the effects of the compounds as inhibitors of the MAPK pathway.

(a) Assay to Detect MEK Inhibition

To evaluate inhibitors of the MAPK pathway, a coupled assay was carried out which measures phosphorylation of serine/threonine residues present in the substrate in the presence or absence of inhibitor. Recombinant glutathione S-transferase fusion protein containing human p45MEK1 (GST-MEK) was activated by c-raf (Sf9 insect cell lysate from triple baculoviral infection with c-raf/ras/lck) and used for the assay. Active GST-MEK was first used to activate a recombinant glutathione S-transferase fusion protein containing p44MAP kinase (GST-MAPK) in the presence of ATP and $Mg^{2+}$ for 60 minutes at room temperature in the presence or absence of potential inhibitors. The activated GST-MAPK was then incubated with myelin basic protein (MBP) as substrate for 10 minutes at room temperature in the presence of ATP, $Mg^{2+}$ and $^{33}P$-ATP. The reaction was stopped by addition of 20% v/v phosphoric acid. Incorporation of $^{33}P$ into the myelin basic protein was determined by capture of the substrate on a filter mat, washing and counting using scintillation methods. The extent of inhibition was determined by comparison with untreated controls.

The final assay solution contained 10 mM Tris, pH 7.5, 0.05 mM EGTA, 8.33 µM [$\gamma^{33}P$]ATP, 8.33 mM $Mg(OAc)_2$, 0.5 mM sodium orthovanadate, 0.05% w/v BSA, 6.5 ng GST-MEK, 1 µg GST-MAPK and 16.5 µg MBP in a reaction volume of 60 µl.

(b) In Vitro MAP Kinase Assay

To determine whether compounds were inhibiting GST-MEK or GST-MAPK, a direct assay of MAPK activity was employed. GST-MAPK was activated by a constitutively active GST-MEK fusion protein containing two point mutations (S217E, S221E) and used for the assay in the presence and absence of potential inhibitors. The activated GST-MAPK was incubated with substrate BP) for 60 min at room temperature in the presence of ATP, $Mg^{2+}$ and $^{33}P$-ATP. The reaction was stopped by addition of 20% v/v phosphoric acid. Incorporation of $^{33}P$ into the myelin basic protein was determined by capture of the substrate on a filter mat, washing and counting using scintillation methods.

The final assay solution contained 12 mM Tris, pH 7.5, 0.06 mM EGTA, 30 µM [$\gamma^{33}P$]ATP, 10 mM $Mg(OAc)_2$, 0.6 mM sodium orthovanadate, 0.06% w/v BSA, 28 ng GST-MAPK and 16.5 µg MBP in a reaction volume of 60 µl.

(c) Cell Proliferation Assays

Cells were seeded into multi-well plates at 20,000–40,000 cells/ml in growth medium containing 5% FCS and incubated overnight at 37° C. The compounds were prepared in fresh medium at an appropriate concentration and added to the wells containing the cells. These were then incubated for a further 72 hours. Cells were then either removed from the wells by incubating with trypsin/EDTA and counted using a Coulter counter, or treated with XIT/PMS in PBSA and optical densities read at 450 nm.

The following assays can be used to measure the effects of the compounds of the present invention as c-Src tyrosine kinase inhibitors, as inhibitors in vitro of the proliferation of c-Src transfected fibroblast cells, as inhibitors in vitro of the migration of A549 human lung tumour cells and as inhibitors in vivo of the growth in nude mice of xenografts of A549 tissue.

(d) In Vitro Src Enzyme Assay

The ability of test compounds to inhibit the phosphorylation of a tyrosine containing polypeptide substrate by the enzyme c-Src kinase was assessed using a conventional Elisa assay.

A substrate solution [100 µl of a 20 µg/ml solution of the polyamino acid Poly(Glu, Tyr) 4:1 (Sigma Catalogue No. P0275) in phosphate buffered saline (PBS) containing 0.2 mg/ml of sodium azide] was added to each well of a number of Nunc 96-well immunoplates (Catalogue No. 439454) and the plates were sealed and stored at 4° C. for 16 hours. The excess of substrate solution was discarded, and aliquots of Bovine Serum Albumin (BSA; 150 µl of a 5% solution in PBS) were transferred into each substrate-coated assay well and incubated for 1 hour at ambient temperature to block non specific binding. The assay plate wells were washed in turn with PBS containing 0.05% v/v Tween 20 (PBST) and with Hepes pH7.4 buffer (50 mM, 300 µl/well) before being blotted dry.

Each test compound was dissolved in dimethyl sulphoxide and diluted with distilled water to give a series of dilutions (from 100 µM to 0.001 µM). Portions (25 µl) of each dilution of test compound were transferred to wells in the washed assay plates. "Total" control wells contained diluted DMSO instead of compound. Aliquots (25 µl) of an aqueous magnesium chloride solution (80 mM) containing adenosine-5'-triphosphate (ATP; 40 µM) was added to all test wells except the "blank" control wells which contained magnesium chloride without ATP.

Active human c-Src kinase (recombinant enzyme expressed in Sf9 insect cells; obtained from Upstate Biotechnology Inc. product 14-117) was diluted immediately prior to use by a factor of 1:10,000 with an enzyme diluent which comprised 100 mM Hepes pH7.4 buffer, 0.2 mM sodium orthovanadate, 2 mM dithiothreitol and 0.02% BSA. To start the reactions, aliquots (50 µl) of freshly diluted enzyme were added to each well and the plates were incubated at ambient temperature for 20 minutes. The supernatant liquid in each well was discarded and the wells were washed twice with PBST. Mouse IgG anti-phosphotyrosine antibody (Upstate Biotechnology Inc. product 05-321; 100 µl) was diluted by a factor of 1:6000 with PBST containing 0.5% w/v BSA and added to each well. The plates were incubated for 1 hour at ambient temperature. The supernatant liquid was discarded and each well was washed with PBST (x4). Horse radish peroxidase (HRP)-linked sheep anti-mouse Ig antibody (Amersham Catalogue No. NXA 931; 100 µl) was diluted by a factor of 1:500 with PBST containing 0.5% w/v BSA and added to each well. The plates were incubated for 1 hour at ambient temperature. The supernatant liquid was discarded and the wells were washed with PBST (x4).

A PCSB capsule (Sigma Catalogue No. P4922) was dissolved in distilled water (100 ml) to provide phosphate-citrate pH5 buffer (50 mM) containing 0.03% sodium perborate. An aliquot (50 ml) of this buffer was mixed with a 50 mg tablet of 2,2'-azinobis(3-ethylbenzothiazoline-6-sulphonic acid) (ABTS; Boehringer Catalogue No. 1204 521). Aliquots (100 µl) of the resultant solution were added to each well. The plates were incubated for 20 to 60 minutes at ambient temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibition of enzyme activity.

(e) In Vitro c-Src Transfected NIH 3T3 (c-src 313) Fibroblast Proliferation Assay This assay determined the ability of a test compound to inhibit the proliferation of National Institute of Health (NIH) mouse 3T3 fibroblast cells that had been stably-transfected with an activating mutant (Y530F) of human c-Src.

Using a similar procedure to that described by Shalloway et al., Cell 1987, 49, 65–73, NIH 3T3 cells were transfected with an activating mutant (Y530F) of human c-Src. The resultant c-Src 3T3 cells were typically seeded at $1.5 \times 10^4$ cells per well into 96-well tissue-culture-treated clear assay plates (Costar) each containing an assay medium comprising Dulbecco's modified Eagle's medium (DMEM; Sigma) plus 0.5% foetal calf serum (FCS), 2 mM glutamine, 100 units/ml penicillin and 0.1 mg/ml streptomycin in 0.9% aqueous sodium chloride solution. The plates were incubated overnight at 37° C. in a humidified (7.5% $CO_2$: 95% air) incubator.

Test compounds were solubilised in DMSO to form a 10 mM stock solution. Aliquots of the stock solution were diluted with the DMEM medium described above and added to appropriate wells. Serial dilutions were made to give a range of test concentrations. Control wells to which test compound was not added were included on each plate. The plates were incubated overnight at 37° C. in a humidified (7.5% $CO_2$: 95% air) incubator.

BrdU labelling reagent Boehringer Mannheim Catalogue No. 647 229) was diluted by a factor of 1:100 in DMEM medium containing 0.5% FCS and aliquots (20 µl) were added to each well to give a final concentration of 10 µM). The plates were incubated at 37° C. for 2 hours. The medium was decanted. A denaturating solution (FixDenat solution, Boehringer Mannheim Catalogue No. 647 229; 50 µl) was added to each well and the plates were placed on a plate shaker at ambient temperature for 45 minutes. The supernatant was decanted and the wells were washed with PBS (200 µper well). Anti-BrdU-Peroxidase solution (Boehringer Mannheim Catalogue No. 647 229) was diluted by a factor of 1:100 in PBS containing 1% BSA and 0.025% dried skimmed milk (Mavel (registered trade mark), Premier Beverages, Stafford, GB) and an aliquot (100 µl) of the resultant solution was added to each well. The plates were placed on a plate shaker at ambient temperature for 90 minutes. The wells were washed with PBS (x5) to ensure removal of non-bound antibody conjugate. The plates were blotted dry and tetramethylbenzidine substrate solution (Boehringer Mannheim Catalogue No. 647 229; 100 µl) was added to each well. The plates were gently agitated on a plate shaker while the colour developed during a 10 to 20 minute period. The absorbance of the wells was measured at 690 nm. The extent of inhibition of cellular proliferation at a range of concentrations of each test compound was determined and an anti-proliferative $IC_{50}$ value was derived.

(f) In Vitro Microdroplet Migration Assay

This assay determines the ability of a test compound to inhibit the migration of adherent mammalian cell lines, for example the human tumour cell line A549.

RPMI medium (Sigma) containing 10% FCS, 1% L-glutamine and 0.3% agarose (Difco Catalogue No. 0142-01) was warmed to 37° C. in a water bath. A stock 2% aqueous agar solution was autoclaved and stored at 42° C. An aliquot (1.5 ml) of the agar solution was added to RPMI medium (10 ml) immediately prior to its use. A549 cells (Accession No. ATCC CCL185) were suspended at a concentration of $2 \times 10^7$ cells/ml in the medium and maintained at a temperature of 37° C.

A droplet (2 µl) of the cell/agarose mixture was transferred by pipette into the centre of each well of a number of 96-well, flat bottomed non-tissue-culture-treated microtitre plate (Bibby Sterilin Catalogue No. 642000). The plates were placed briefly on ice to speed the gelling of the agarose-containing droplets. Aliquots (90 µl) of medium which had been cooled to 4° C. were transferred into each well, taking care not to disturb the microdroplets. Test compounds were diluted from a 10 mM stock solution in DMSO using RPMI medium as described above. Aliquots (10 µl) of the diluted test compounds were transferred to the wells, again taking care not to disturb the microdroplets. The plates were incubated at 37° C. in a humidified (7.5% $CO_2$: 95% air) incubator for about 48 hours.

Migration was assessed visually and the distance of migration was measured back to the edge of the agar droplet. A migratory inhibitory $IC_{50}$ was derived by plotting the mean migration measurement against test compound concentration.

(g) In Vivo A549 Xenograft Growth Assay

This test measures the ability of compounds to inhibit the growth of the A549 human carcinoma grown as a tumour in athymic nude mice (Alderley Park nu/nu strain). A total of about $5 \times 10^6$ A549 cells in matrigel (Beckton Dickinson Catalogue No. 40234) were injected subcutaneously into the left flank of each test mouse and the resultant tumours were allowed to grow for about 14 days. Tumour size was measured twice weekly using callipers and a theoretical volume was calculated. Animals were selected to provide control and treatment groups of approximately equal average tumour volume. Test compounds were prepared as a ball-milled suspension in 1% polysorbate vehicle and dosed orally once daily for a period of about 28 days. The effect on tumour growth was assessed.

Although the pharmacological properties of the compounds of the Formula I vary with structural change as expected, in general activity possessed by compounds of the Formula I, may be demonstrated at the following concentrations or doses in one or more of the above tests (a) to (g):

Test (a): $IC_{50}$ in the range, for example, less than 4 µM;
Test (b): activity was observed in this screen;
Test (c): $IC_{50}$ in the range, for example, less than 30 µM.
Test (d): $IC_{50}$ in the range, for example, 0.001–10 µM;
Test (d): $IC_{50}$ in the range, for example, 0.01–20 µM;
Test (f): activity in the range, for example, 0.1–25 µM;
Test (g): activity in the range, for example, 1–200 mg/kg/day;

No physiologically-unacceptable toxicity was observed in Test (g) at the effective dose for compounds tested of the present invention. Accordingly no untoward toxicological effects are expected when a compound of Formula I, or a pharmaceutically-acceptable salt thereof, as defined hereinbefore is administered at the dosage ranges defined hereinafter.

According to a further aspect of the invention there is provided a pharmaceutical composition which comprises a quinoline derivative of the Formula I, or a pharmaceutically-acceptable salt thereof as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

According to a further aspect of the invention there is provided a quinoline derivative of the Formula I, or a pharmaceutically-acceptable salt thereof, as defined hereinbefore for use in a method of treatment of the human or animal body by therapy.

As stated above we have also found that the quinoline derivatives of the present invention of Formula I possess potent anti-tumour activity which it is believed is obtained by way of inhibition of one or more of the MEK enzymes that are involved in the MAPK pathway.

Accordingly, the quinoline derivatives of Formula I are of value as anti-proliferative agents in the containment and/or treatment of solid tumour disease. Particularly, the compounds of Formula I are expected to be useful in the prevention or treatment of those tumours which are sensitive to inhibition of one or more of the MEK enzymes that are involved in the MAPK pathway. Further, the compounds of Formula I are expected to be useful in the prevention or treatment of those tumours which are mediated alone or in part by inhibition of the MEK enzymes i.e. the compounds may be used to produce a MEK enzyme inhibitory effect in a warm-blooded animal in need of such treatment. Specifically, the compounds of Formula I are expected to be useful in the prevention or treatment of solid tumour disease.

Thus, according to this aspect of the invention there is provided of a quinoline derivative of the Formula I, or a pharmaceutically-acceptable salt thereof, as defined hereinbefore for use as an anti-proliferative agent in the containment and/or treatment of solid tumour disease.

According to a further aspect of the invention there is provided the use of a quinoline derivative of the Formula I, or a pharmaceutically-acceptable salt thereof as defined hereinbefore in the manufacture of a medicament for use as an anti-proliferative agent in the containment and/or treatment of solid tumour disease.

According to a further feature of the invention there is provided a method for producing an anti-proliferative effect by the containment and/or treatment of solid tumour disease in a warm-blooded animal, such as man, in need of such treatment which comprises administering to said animal an effective amount of a quinoline derivative of the Formula I, or a pharmaceutically-acceptable salt thereof, as defined hereinbefore.

According to a further aspect of the invention there is provided the use of a quinoline derivative of the Formula I, or a pharmaceutically-acceptable salt thereof as defined hereinbefore in the manufacture of a medicament for use in the prevention or treatment of solid tumour disease in a warm-blooded animals such as man.

According to a further feature of this aspect of the invention there is provided a method for the prevention or treatment of solid tumour disease in a warm-blooded animal, such as man, in need of such treatment which comprises administering to said animal an effective amount of a quinoline derivative of the Formula I, or a pharmaceutically-acceptable salt thereof, as defined hereinbefore.

According to a further aspect of the invention there is provided the use of a quinoline derivative of the Formula I, or a pharmaceutically-acceptable salt thereof as defined hereinbefore in the manufacture of a medicament for use in the prevention or treatment of those tumours which are sensitive to inhibition of MEK enzymes that are involved in the MAPK pathway. Particular enzymes that the tumours may be sensitive to are MEK 1, MEK 2 and MEK 5.

According to a further feature of this aspect of the invention there is provided a method for the prevention or treatment of those tumours which are sensitive to inhibition of MEK enzymes that are involved in the MAPK pathway which comprises administering to said animal an effective amount of a quinoline derivative of the Formula I, or a pharmaceutically-acceptable salt thereof, as defined hereinbefore.

According to a further aspect of the invention there is provided the use of a quinoline derivative of the Formula I, or a pharmaceutically-acceptable salt thereof, as defined hereinbefore in the manufacture of a medicament for use in providing a MEK enzyme inhibitory effect According to a further feature of this aspect of the invention there is provided a method for providing a MEK enzyme inhibitory effect which comprises administering to said animal an effective amount of a quinoline derivative of the Formula I, or a pharmaceutically-acceptable salt thereof as defined hereinbefore.

We have also found that the quinoline derivatives of the present invention possess potent anti-tumour activity which it is believed is obtained by way of inhibition of one or more of the non-receptor tyrosine-specific protein kinases such as c-Src kinase that are involved in the signal transduction steps which lead to the invasiveness and migratory ability of metastasising tumour cells.

Particularly, the quinoline derivatives of the present invention are of value as anti-invasive agents in the containment and/or treatment of solid tumour disease. Particularly, the compounds of the present invention are expected to be useful in the prevention or treatment of those tumours which are sensitive to inhibition of one or more of the multiple non-receptor tyrosine kinases such as c-Src kinase that are involved in the signal transduction steps which lead to the invasiveness and migratory ability of metastasising tumour cells. Further, the compounds of the present invention are expected to be useful in the prevention or treatment of those tumours which are mediated alone or in part by inhibition of the enzyme c-Src, i.e. the compounds may be used to produce a c-Src enzyme inhibitory effect in a warm-blooded animal in need of such treatment Specifically, the compounds of the present invention are expected to be useful in the prevention or treatment of solid tumour disease.

According to this aspect of the invention there is provided a quinoline derivative of the Formula I, or a pharmaceutically-acceptable salt thereof, as defined hereinbefore for use as an anti-invasive agent in the containment and/or treatment of solid tumour disease.

According to a further feature of this aspect of the invention there is provided the use of a quinoline derivative of the Formula I, or a pharmaceutically-acceptable salt thereof, as defined hereinbefore in the manufacture of a medicament for use as an anti-invasive agent in the containment and/or treatment of solid tumour disease.

According to a further feature of this aspect of the invention there is provided a method for producing an anti-invasive effect by the containment and/or treatment of solid tumour disease in a warm-blooded animal, such as man, in need of such treatment which comprises administering to said animal an effective amount of a quinoline derivative of the Formula I, or a pharmaceutically-acceptable salt thereof, as defined hereinbefore.

According to a further aspect of the invention there is provided the use of a quinoline derivative of the Formula I, or a pharmaceutically-acceptable salt thereof as defined hereinbefore in the manufacture of a medicament for use in the prevention or treatment of those tumours which are sensitive to inhibition of non-receptor tyrosine kinases such as c-Src kinase that are involved in the signal transduction steps which lead to the invasiveness and migratory ability of metastasising tumour cells.

According to a further feature of this aspect of the invention there is provided a method for the prevention or treatment of those tumours which are sensitive to inhibition of non-receptor tyrosine kinases such as c-Src kinase that are involved in the signal transduction steps which lead to the invasiveness and migratory ability of metastasising tumour cells which comprises administering to said animal an effective amount of a quinoline derivative of the Formula I, or a pharmaceutically-acceptable salt thereof, as defined hereinbefore.

According to a further aspect of the invention there is provided the use of a quinoline derivative of the Formula I, or a pharmaceutically-acceptable salt thereof, as defined hereinbefore in the manufacture of a medicament for use in providing a c-Src kinase inhibitory effect.

According to a further feature of this aspect of the invention there is provided a method for providing a c-Src kinase inhibitory effect which comprises administering to said animal an effective amount of a quinoline derivative of the Formula I, or a pharmaceutically-acceptable salt thereof, as defined hereinbefore.

The anti-proliferative and anti-invasive treatment defined hereinbefore may be applied as a sole therapy or may involve, in addition to the quinoline derivative of the invention, conventional surgery or radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5 α-reductase such as finasteride;

(iii) other anti-invasion agents (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinoline derivative of the formula I as defined hereinbefore and an additional anti-tumour agent as defined hereinbefore for the conjoint treatment of cancer.

Although the compounds of the Formula I are primarily of value as therapeutic agents for use in warm-blooded animals (including man), they are also useful whenever it is required to inhibit the effects of the MEK enzymes that are involved in the MAPK kinase pathway or the effects of c Src. Thus, they are useful as pharmacological standards for use in the development of new biological tests and in the search for new pharmacological agents.

The invention will now be illustrated in the following Examples in which, generally:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (EPLC) was performed on C18 reverse phase silica, for example on a Dynamax C-18 60 Å preparative reversed-phase column;

(iv) yields, where present, are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Metder SP62 automatic melting point apparatus or an oil-bath apparatus; melting points for the end-products of the Formula I were determined after crystallisation from a conventional organic solvent such as ethanol, methanol, acetone, ether or hexane, alone or in admixture;

(viii) where certain compounds were obtained as an acid-addition salt, for example a mono hydrochloride salt or a dihydrochloride salt, the stoichiometry of the salt was based on the number and nature of the basic groups in the compound, the exact stoichiometry of the salt was generally not determined, for example by means of elemental analysis data;

(ix) the following abbreviations have been used:
DMF N,N-dimethylformamide
DMSO dimethylsulphoxide
TBE tetrahydrofuran

EXAMPLE 1

3-cyano-6-methoxy-7-[3-(4-methylpiperazin-1-yl) propoxy]-4-[4-(3-methoxyprop-1-ynyl)benzofuran-7-ylamino]quinoline Sodium hexamethyldisilazane (1M solution in THF; 0.63 ml) was added to a mixture of [4-(3-methoxyprop-1-ynyl) benzofuran-7-yl]amine (0.06 g) and 4-chloro-3-cyano-6-methoxy-7-[3-(4-methylpiperazin-1-yl)propoxy]quinoline (0.106 g) in DMF (5 ml) that was cooled to 0° C. The resultant mixture was stirred and allowed to warm to ambient temperature for 16 hours. The reaction mixture was reduced in vacuo and partitioned between ethylacetate and water. The organics were washed with water, saturated brine and dried with magnesium sulfate. The solvent was removed in vacuo and the residue purified by column chromatography on silica using a gradient of 0–10% methanol/dichloromethane as eluent. The product fractions were combined and reduced in vacuo and the residue dissolved in minimal dichloromethane, diluted with diethyl ether and precipitated as an HCl salt by the addition of 1.0M ethereal HCl. The resultant solid was centrifuged and washed with diethyl ether (X3) and dried to give the title compound as a yellow solid. (0.077 g); NMR Spectrum: (DMSOd$_6$ @ 373K) 2.30 (m, 2H), 2.80 (s, 3H), 3.15–3.20 (m, 2H), 3.36–3.50 (m, 11H), 4.02 (s, 3H), 4.37 (t, 2H), 4.45 (s, 2H), 7.01 (s, 1H), 7.35 (d, 1H), 7.44 (d, 1H), 7.59 (s, 1H), 8.00 (s, 1H), 8.11 (s, 1H), 8.65 (s, 1H); Mass Spectrum: M+H$^+$ 540.14.

The [4-(3-methoxyprop-1-ynyl)benzofuran-7-yl]amine used as a starting material was prepared as follows:

Bis(Triphenyl-phosphine)palladium(II) chloride (144 mg), copper iodide (58 mg) and diisopropylamine (208 mg) were added to a stirred solution of (4-Iodo-7-amino-benzfuran) (266 mg) and methyl propargyll ether (144 mg) in ethyl acetate (5 mls) at −20° C. The reaction was allowed to warm to ambient temperature over 16 hours. The reaction mixture was partitioned between ethyl acetate and saturated NaHCO$_3$. The organics were washed with saturated NaHCO$_3$, water and saturated brine and dried over magnesium sulfate. The product was purified by column chromatography on silica using 100% dichloromethane as eluent. [4-(3-methoxyprop-1-ynyl)benzofuran-7-yl]amine was thus obtained as a yellow/brown gum (70 mg); NMR Spectrum: (DMSOd$_6$) 3.34 (s, 3H), 4.34 (s, 2H), 5.74 (s, 2H), 6.50 (d, 1H), 6.80 (s, 1H), 7.05 (d, 1H), 7.96, s, 1H); Mass Spectrum: M+H$^+$ mass ion not observed.

Benzyltrimethylammonium dichloroiodate (0.58 g) was added portionwise over 10 minutes to a stirred mixture of 1-benzofuran-7-amine (0.2 g), calcium carbonate (0.195 g) in methanol (1.5 ml) and dichloromethane (3 ml). The reaction mixture was stirred at ambient temperature for 1.5 hours. The reaction mixture was diluted with water and extracted with dichloromethane. The organics were washed with water, saturated brine and dried over magnesium sulfate. The residue was purified by column chromatography on silica using a gradient of an 8:1 mixture of dichloromethane/isohexane to dichloromethane as eluent There was thus obtained 4-iodo-7-aminobenzfuran as a beige crystalline solid (0.266 g); NMR Spectrum: (DMSOd$_6$) 5.47 (bs, 2H); 6.41 (d, 1H); 6.58 (d, 1H), 7.24 (d, 1H), 7.97, (d, 1H). M+H$^+$ mass ion not observed.

The 4-chloro-3-cyano-6-methoxy-7-[3-(4-methylpiperazin-1-yl)propoxy]quinoline used as a starting material was prepared as follows:

A mixture of 3-bromopropanol (20 ml), N-methylpiperazine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation at about 60–70° C. under about 0.2 mm Hg to give 1-(3-hydroxypropyl)-4-methylpiperazine (17 g); NMR Spectrum: (CDCl$_3$) 1.72 (m, 2H), 2.3 (s, 3H), 2.2–2.8 (m, 8H), 2.6 (t, 2H), 3.8 (t, 2H), 5.3 (br s, 1H).

A solution of diisopropyl azodicarboxylate (12.1 ml) in methylene chloride (50 ml) was added dropwise during 30 minutes to a stirred mixture of 4-chloro-3-cyano-7-hydroxy-6-methoxyquinoline (12 g), 1-(3-hydroxypropyl)-4-methylpiperazine (9.7 g), triphenylphosphine (16.1 g) and methylene chloride (200 ml) that had been cooled to 5° C. The resultant mixture was allowed to warm to ambient temperature and was then stirred for 1 hour. Further portions of diisopropyl azodicarboxylate (1.2 ml) and triphenylphosphine (1.6 g) were added and the mixture was stirred at ambient temperature for a further 1 hour. The mixture was poured into water and the organic layer was separated, washed with a saturated brine solution, dried over magnesium sulphate and evaporated. The material so obtained was purified by column chromatography on silica using increasingly polar mixtures of methylene chloride and methanol as eluent. There was thus obtained the required starting material as a solid (14.5 g); NMR Spectrum: (DMSOd$_6$) 1.95 (m, 2H), 2.13 (s, 3H), 2.24–2.5 (m, 10H), 4.0 (s, 3H), 4.25 (t, 2H), 7.43 (s, 1H), 7.51 (s, 1H), 8.95 (s, 1H); Mass Spectrum: M+H$^+$ 375 and 377.

EXAMPLE 2

3-Cyano-6,7-dimethoxy-4-[4-(2-methoxycarbonylvinyl)benzofuran-7-ylamino]quinoline The 3-cyano-6,7-dimethoxy-4-(4-iodobenzofuran-7-ylamino)quinoline (0.275 g) was suspended in N,N-dimethylformamide (15 ml) in a nitrogen-flushed vessel, then palladium (II) acetate (16 mg) was added, followed by methyl acrylate (1.1 ml) and triethylamine (0.6 ml). The reaction was heated to 115° C. for 5 hours before filtration and evaporation of solvents under reduced pressure. The residue was purified by column chromatography on silica using increasingly polar mixtures of iso-hexane with ethyl acetate as eluent The resulting product was triturated with diethyl ether and filtered. There was thus obtained the title compound (0.203 g), as a yellow solid; NMR Spectrum: (DMSOd$_6$) 3.77 (s, 3H), 3.94 (s, 3H), 3.99 (s, 3H), 6.73 (d, 1H), 7.31 (d, 1H), 7.40(s, 1H), 7.47 (d, 1H), 7.76 (d, 1H), 7.86 (s, 1H), 7.97 (d, 1H), 8.08 (d, 1H), 8.56 (s, 1H), 10.02 (br s, 1H); Mass Spectrum: M+H$^+$ 430.

What is claimed is:

1. A quinoline derivative of the Formula I

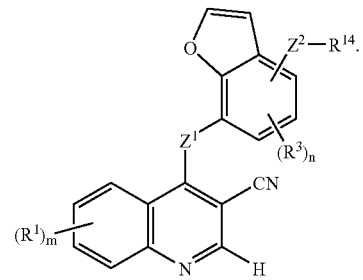

wherein $Z^1$ is an O, S, SO, SO$_2$, N(R$^2$) or C(R$^2$)$_2$ group, wherein each R$^2$ group, which may be the same or different, is hydrogen or (1–6C)alkyl;

m is 0, 1, 2, 3 or 4;

each R$^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

$Q^1$-$X^1$— wherein $X^1$ is a direct bond or is selected from O, S, SO, SO$_2$, N(R$^4$), CO, CH(OR$^4$), CON(R$^4$), N(R$^4$)CO, SO$_2$N(R$^4$), N(R$^4$)SO$_2$, OC(R$^4$)$_2$, SC(R$^4$)$_2$ and N(R$^4$)C(R$^4$)$_2$, wherein R$^4$ is hydrogen or (1–6C)alkyl, and Q$^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or (R$^1$)$_m$ is (1–3C)alkylenedioxy, and wherein adjacent carbon atoms in any (2–6C)alkylene chain within a R$^1$ substituent are optionally separated by the insertion into the chain of a group selected from O, S, SO, SO$_2$, N(R$^5$), CO, CH(OR$^5$), CON(R$^5$), N(R$^5$)CO, SO$_2$N(R$^5$), N(R$^5$)SO$_2$, CH═CH and C≡C wherein R$^5$ is hydrogen or (1–6C)alkyl or, when the inserted group is N(R$^5$), R$^5$ may also be (2–6C)alkanoyl, and wherein any CH$_2$═CH— or HC≡C— group within a R$^1$ substituent optionally bears at the terminal CH$_2$═ or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl, di-[(1–6C)alkyl]amino-(1–6C)alkyl or from a group of the formula:

$Q^2$-$X^2$— wherein $X^2$ is a direct bond or is selected from CO and $N(R^6)CO$, wherein $R^6$ is hydrogen or (1–6C)alkyl, and $Q^2$ is aryl, aryl-(1–6C)alkyl, heteroaryl, heteroaryl-(1–6C)alkyl, heterocyclyl or heterocyclyl-(1–6C)alkyl, and wherein any CH, $CH_2$ or $CH_3$ group within a $R^1$ substituent optionally bears on each said CH, $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

—$X^3$-$Q^3$ wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

—$X^4$—$R^8$ wherein $X^4$ is a direct bond or is selected from O and $N(R^9)$, wherein $R^9$ is hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl or from a group of the formula:

—$X^5$-$Q^4$ wherein $X^5$ is a direct bond or is selected from O, $N(R^{10})$ and CO, wherein $R^{10}$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and wherein any heterocyclyl group within a substituent on $R^1$ optionally bears 1 or 2 oxo or thioxo substituents;

n is 0, 1, 2 or 3;

each $R^3$ group is halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

—$X^6$—$R^{11}$ wherein $X^6$ is a direct bond or is selected from O and $N(R^{12})$, wherein $R^{12}$ is hydrogen or (1–6C)alkyl, and $R^{11}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl;

$Z^2$ is a C≡C or $C(R^{13})$=$C(R^{13})$ group, wherein each $R^{13}$ group, which may be the same or different, is hydrogen or (1–6C)alkyl; and $R^{14}$ is selected from halogeno, cyano, isocyano, formyl, carboxy, carbamoyl, (2–8C)alkenyl, (2–8C)alkynyl, (1–6C)alkoxycarbonyl, N-(1–6C)alkylcarbamoyl, N,N-di-[(1–6C)alkyl]carbamoyl, (2–6C)alkanoyl, N-(1–6C)alkylsulphamoyl, N,N-di-[(1–6C)alkyl]sulphamoyl, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl or from a group of the formula:

—$X^7$-$Q^5$ wherein $X^7$ is a direct bond or is selected from CO, $CH(OR^{15})$, $CON(R^{15})$ or $SO_2N(R^{15})$, wherein $R^{15}$ is hydrogen or (1–6C)alkyl, and $Q^5$ is aryl, aryl-(1–6C)alkyl, (3–7C)cycloalkyl, (3–7C)cycloalkyl-(1–6C)alkyl, heteroaryl, heteroaryl-(1–6C)alkyl, heterocyclyl or heterocyclyl-(1–6C)alkyl, and wherein any CH, $CH_2$ or $CH_3$ group within a $R^{14}$ substituent optionally bears on each said CH, $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

—$X^8$-$Q^6$ wherein $X^8$ is a direct bond or is selected from O, S, SO, $SO_2$, $N(R^{16})$, CO, $CH(OR^6)$, $CON(R^{16})$, $N(R^{16})CO$, $SO_2N(R^{16})$, $N(R^{16})SO_2$, $C(R^{16})_2O$, $C(R^{16})_2S$ and $N(R^{16})C(R^{16})_2$, wherein $R^{16}$ is hydrogen or (1–6C)alkyl, and $Q^6$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^{14}$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino, N-(1–6C)alkyl-(1–6C)alkanesulphonylamino or from a group of the formula:

$$—X^9—R^{17}$$

wherein $X^9$ is a direct bond or is selected from O and $N(R^{18})$, wherein $R^{18}$ is hydrogen or (1–6C)alkyl, and $R^{17}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl, or from a group of the formula:

$$—X^{10}-Q^7$$

wherein $X^{10}$ is a direct bond or is selected from O, $N(R^{19})$ and CO, wherein $R^{19}$ is hydrogen or (1–6C)alkyl, and $Q^7$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and wherein any heterocyclyl group within a substituent on $R^{14}$ optionally bears 1 or 2 oxo or thioxo substituents;

or a pharmaceutically-acceptable salt thereof.

2. A quinoline derivative of the Formula I or a pharmaceutically acceptable salt thereof, according to claim 1 wherein $R^1$, $R^2$, $R^3$, $Z^1$, $Z^2$, m and n have any of the meanings defined in claim 1 and $R^{14}$ is selected from halogeno, cyano, formyl, carboxy, carbamoyl, (1–6C)alkoxycarbonyl, N-(1–6C)alkylcarbamoyl, N,N-di-[(1–6C)alkyl]carbamoyl, (2–6C)alkanoyl, N-(1–6C)alkylsulphamoyl, N,N-di-[(1–6C)alkyl]sulphamoyl, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or from a group of the formula:

$$—X^7-Q^5$$

wherein $X^7$ is a direct bond or CO and $Q^5$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a $R^{14}$ substituent optionally bears on each said $CH_2$ or $CH_3$ group one or more halogeno or (1–6C)alkyl substituents or a substituent selected from hydroxy, cyano, amino, (1–6C)alkoxy, (1–6C)alkylthio, (1–6C)alkylsulphinyl, (1–6C)alkylsulphonyl, (1–6C)alkylamino, di-[(1–6C)alkyl]amino, (2–6C)alkanoyl, (2–6C)alkanoyloxy, (2–6C)alkanoylamino, N-(1–6C)alkyl-(2–6C)alkanoylamino or from a group of the formula:

$$—X^8-Q^6$$

wherein $X^8$ is a direct bond or is selected from O, $N(R^{16})$, $CON(R^6)$, $N(R^{16})CO$ and $C(R^6)_2O$, wherein $R^{16}$ is hydrogen or (1–6C)alkyl, and $Q^6$ is heteroaryl, heteroaryl-(1–6C)alkyl, heterocyclyl or heterocyclyl-(1–6C)alkyl, and wherein any aryl, heteroaryl or heterocyclyl group within a substituent on $R^{14}$ optionally bears 1, 2 or 3 substituents, which may be the same or different, selected from halogeno, trifluoromethyl, hydroxy, amino, carbamoyl, (1–6C)alkyl, (2–8C)alkenyl, (2–8C)alkynyl, (1–6C)alkoxy, (1–6C)alkylsulphonyl, N-(1–6C)alkylcarbamoyl, N,N-di-[(1–6C)alkyl]carbamoyl and (2–6C)alkanoyl, or optionally bears 1 substituent selected from a group of the formula:

$$—X^9—R^{17}$$

wherein $X^9$ is a direct bond or is selected from O and $N(R^{18})$, wherein $R^{18}$ is hydrogen or (1–6C)alkyl, and $R^{17}$ is hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl, (1–6C)alkoxycarbonylamino-(1–6C)alkyl, and from a group of the formula:

$$—X^{10}-Q^7$$

wherein $X^{10}$ is a direct bond or is selected from O, $N(R^{19})$ and CO, wherein $R^{19}$ is hydrogen or (1–6C)alkyl, and $Q^7$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^{14}$ optionally bears 1 or 2 oxo substituents.

3. A quinoline derivative of the Formula I according to claim 1 wherein:

$Z^1$ is O or NH;

m is 1 and the $R^1$ group is located at the 5-, 6- or 7-position or m is 2 and each $R^1$ group, which may be the same or different, is located at the 5- and 7-positions or at the 6- and 7-positions and $R^1$ is selected from hydroxy, amino, methyl, ethyl, propyl, butyl, methoxy, ethoxy, propoxy, isopropoxy, butoxy, pent-4-ynyloxy, hex-5-ynyloxy, methylamino, ethylamino, dimethylamino, diethylamino, acetamido, propionamido, 2-imidazol-1-ylethoxy, 2-(1,2,4-triazol-1-yl)ethoxy, tetrahydrofuran-3-yloxy, tetrahydropyran-4-yloxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-piperazin-1-ylethoxy, 3-piperazin-1-ylpropoxy, 4-piperazin-1-ylbutoxy, 2-homopiperazin-1-ylethoxy and 3-homopiperazin-1-ylpropoxy, and wherein adjacent carbon atoms in any (2–6C)alkylene chain within a $R^1$ substituent are optionally separated by the insertion into the chain of a group selected from O, NH, N(Me), CH=CH and C≡C, and wherein any $CH_2$ or $CH_3$ group within a $R^1$ substituent optionally bears on each said $CH_2$ or $CH_3$ group one or more fluoro or chloro groups or a substituent selected from hydroxy, amino, methoxy, methylsulphonyl, methylamino, dimethylamino, diethylamino, N-ethyl-N-methylamino, N-isopropyl-N-methylamino, N-methyl-N-propylamino and acetoxy;

and wherein any heteroaryl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, N-methylcarbamoyl and N,N-dimethylcarbamoyl and a pyrrolidin-2-yl, piperidin-3-yl, piperidin-4-yl, piperazin-1-yl or homopiperazin-1-yl group within a $R^1$ substituent is optionally N-substituted with allyl, methylsulphonyl, acetyl, 2-fluoroethyl, 3-fluoropropyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

n is 0 or 1 and the $R^3$ group, if present, is located at the 5- or 6-position of the benzofuran-7-yl group and is selected from fluoro, chloro, bromo, trifluoromethyl, cyano, hydroxy, methyl, ethyl, vinyl, allyl, ethynyl, methoxy and ethoxy;

$Z^2$ is a C≡C or CH=CH group; and $R^{14}$ is selected from cyano, formyl, carboxy, carbamoyl, methoxycarbonyl, ethoxycarbonyl, N-methylcarbamoyl, N-ethylcarbamoyl, N,N-dimethylcarbamoyl, N-ethyl-N-methylcarbamoyl, N,N-diethylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, cyanomethyl, 2-cyanoethyl, 3-cyanopropyl, methylaminomethyl, ethylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, 2-acetamidoethyl and 3-acetamidopropyl, or from a group of the formula:

—X⁷-Q⁵ wherein $X^7$ is a direct bond or CO and $Q^5$ is 1-pyrrolidinyl, morpholino, 1,1-dioxotetrahydro-4H-1,4-thiazin-4-yl, piperidino, 1-homopiperidinyl, piperazin-1-yl, homopiperazin-1-yl, 1-pyrrolidinylmethyl, morpholinomethyl, piperidinomethyl, 1-homopiperidinylmethyl, 1,1-dioxotetrahydro-4H-1,4-thiazin-4-ylmethyl, piperazin-1-ylmethyl, homopiperazin-1-ylmethyl or 3-morpholinopropyl, and wherein any $CH_2$ or $CH_3$ group within a $R^{14}$ substituent optionally bears on each said $CH_2$ or $CH_3$ group one or more fluoro, chloro or methyl groups or a substituent selected from hydroxy, amino, methoxy, methylamino, dimethylamino, acetoxy, acetamido and N-methylacetamido, and wherein any heterocyclyl group within a substituent on $R^{14}$ optionally bears 1, 2 or 3 substituents, which may be the same or different, selected from hydroxy, amino, carbamoyl, methyl, ethyl allyl 2-propynyl, methoxy, methylsulphonyl, N-methylcarbamoyl, N,N-dimethylcarbamoyl and acetyl, or optionally bears 1 substituent selected from a group of the formula:

—X⁹—R¹⁷ wherein $X^9$ is a direct bond and $R^{17}$ is 2-hydroxyethyl, 3-hydroxypropyl, 2-methoxyethyl, 3-methoxypropyl, cyanomethyl, aminomethyl, methylaminomethyl, dimethylaminomethyl, acetamidomethyl, methoxycarbonylaminomethyl, ethoxycarbonylaminomethyl or tert-butoxycarbonylaminomethyl, and wherein any heterocyclyl group within a substituent on $R^{14}$ optionally bears 1 or 2 oxo substituents;

or a pharmaceutically-acceptable acid-addition salt thereof.

4. A quinoline derivative of the Formula I, or a pharmaceutically acceptable salt thereof, according to claim 1 wherein $R^1$, $R^2$, $R^3$, $R^{14}$, $Z^2$, m and n have any of the meanings defined in claim 1 and $Z^1$ is NH.

5. A quinoline derivative of the Formula I according to claim 1 wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-methylsulphonylethoxy, 3-methylsulphonylpropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy, 2-(2-pyrrolidin-1-ylethoxy)ethoxy, 2-(2-morpholinoethoxy)ethoxy, 2-(2-piperidinoethoxy)ethoxy and 2-[2-(4-methylpiperazin-1-yl)ethoxy]ethoxy;

n is 0 or n is 1 and the $R^3$ group, if present, is located at the 5-position of the benzofuran-7-yl group and is selected from chloro and bromo;

the -$Z^2$-$R^{14}$ group is located at the 4-position on the benzofuran-7-yl group, $Z^2$ is a C≡C or CH=CH group; and $R^{14}$ is selected from cyano, formyl, carboxy, carbamoyl, methoxycarbonyl, ethoxycarbonyl, N-methylcarbamoyl, N-ethylcarbamoyl, N-(2-methoxyethyl)carbamoyl, N,N-dimethylcarbamoyl, N-ethyl-N-methylcarbamoyl, N-(2-methoxyethyl)-N-methylcarbamoyl, acetyl, propionyl, chloromethyl, 2-chloroethyl, 3-chloropropyl, hydroxymethyl, 2-hydroxyethyl, 3-hydroxypropyl, methoxymethyl, 2-methoxyethyl, 3-methoxypropyl, dimethylaminomethyl, 2-dimethylaminoethyl, 3-dimethylaminopropyl, 1-pyrrolidinylcarbonyl, morpholinocarbonyl, 1,1-dioxotetrahydro-4H-1,4-thiazin-4-ylcarbonyl, piperidinocarbonyl, piperazin-1-ylcarbonyl, 1-pyrrolidinylmethyl, morpholinomethyl, piperidinomethyl, 1,1-dioxotetrahydro-4H-1,4-thiazin-4-ylmethyl, piperazin-1-ylmethyl and 3-morpholinopropyl;

or a pharmaceutically-acceptable acid-addition salt thereof.

6. A quinoline derivative of the Formula I according to claim 1 wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy and 2-(2-pyrrolidin-1-ylethoxy)ethoxy;

n is 0 or n is 1 and $R^3$ is a chloro group located at the 5-position of the benzofuran-7-yl group;

the -$Z^2$-$R^{14}$ group is located at the 4-position on the benzofuran-7-yl group, $Z^2$ is a C≡C group; and $R^{14}$ is selected from hydroxymethyl, methoxymethyl, dimethylaminomethyl, 1-pyrrolidinylmethyl, morpholinomethyl, piperidinomethyl, 1,1-dioxotetrahydro-4H-1,4-thiazin-4-ylmethyl and piperazin-1-ylmethyl;

or a pharmaceutically-acceptable acid-addition salt thereof.

7. A quinoline derivative of the Formula I according to claim 1 wherein:

$Z^1$ is NH;

m is 2 and the first $R^1$ group is a 6-methoxy group and the second $R^1$ group is located at the 7-position and is selected from methoxy, ethoxy, 2-fluoroethoxy, 2-chloroethoxy, 3-fluoropropoxy, 3-chloropropoxy, 2-(2-chloroethoxy)ethoxy, 2-(2-methoxyethoxy)ethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 3-(4-allylpiperazin-1-yl)propoxy, 3-(4-methylsulphonylpiperazin-1-yl)propoxy, 3-(4-acetylpiperazin-1-yl)propoxy, 2-(4-cyanomethylpiperazin-1-yl)ethoxy, 3-(4-cyanomethylpiperazin-1-yl)propoxy, 2-[4-(2-fluoroethyl)piperazin-1-yl]ethoxy, 3-[4-(2-fluoroethyl)piperazin-1-yl]propoxy, 2-(3-oxopiperazin-1-yl)ethoxy, 3-(3-oxopiperazin-1-yl)propoxy and 2-(2-pyrrolidin-1-ylethoxy)ethoxy;

n is 0 or n is 1 and $R^3$ is a chloro group located at the 5-position of the 1,3-benziodioxol-4-yl group;

the -$Z^2$-$R^{14}$ group is located at the 4-position on the benzofuran-7-yl group, $Z^2$ is a CH═CH group; and $R^{14}$ is selected from cyano, carboxy, carbamoyl, methoxycarbonyl, ethoxycarbonyl, N-methylcarbamoyl, N-ethylcarbamoyl, N-(2-methoxyethyl)carbamoyl, N,N-dimethylcarbamoyl, N-ethyl-N-methylcarbamoyl, N-(2-methoxyethyl)-N-methylcarbamoyl, acetyl, propionyl, 1-pyrrolidinylcarbonyl, morpholinocarbonyl, 1,1-dioxotetrahydro-4H-1,4-thiazin-4-ylcarbonyl, piperidinocarbonyl and piperazin-1-ylcarbonyl;

or a pharmaceutically-acceptable acid-addition salt thereof.

8. A process for the preparation of a quinoline derivative of the Formula I or a pharmaceutically-acceptable salt thereof, according to claim 1 which comprises:

(a) the reaction of a quinoline of the Formula II

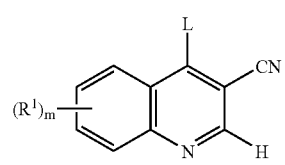

II wherein L is a displaceable group and m and $R^1$ have any of the meanings defined in claim 1 hereinbefore except that any functional group is protected if necessary, with a compound of the Formula III

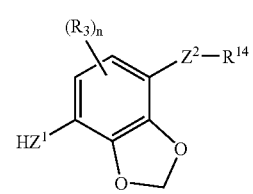

III wherein $Z^1$ is O, S, or N($R^2$) and n, $R^3$, $R^2$, $Z^2$ and $R^{14}$ have any of the meanings defined in claim 1 except that any functional group is protected if necessary, whereafter any protecting group that is present is removed by conventional means;

(b) for the production of those compounds of the Formula I wherein at least one $R^1$ group is a group of the formula $Q^1$-$X^1$— wherein $Q^1$ is an aryl-(1–6C)alkyl, (3–7C)cycloalkyl-(1–6C)alkyl, (3–7C)cycloalkenyl-(1–6C)alkyl, heteroaryl-(1–6C)alkyl or heterocyclyl-(1–6C)alkyl group or an optionally substituted alkyl group and $X^1$ is an oxygen atom, the coupling, conveniently in the presence of a suitable dehydrating agent, of a quinoline of the Formula V

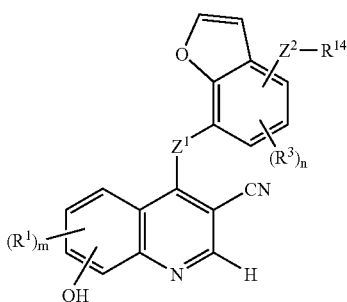

wherein m, $R^1$, $Z^1$, n, $R^3$, $Z^2$ and $R^{14}$ have any of the meanings defined in claim 1, except that any functional group is protected if necessary, with an appropriate alcohol of the formula $Q^1$-OH wherein any functional group is protected if necessary, whereafter any protecting group that is present is removed by conventional means;

(c) for the production of those compounds of the Formula I wherein $R^1$ is an amino-substituted (1–6C)alkoxy group (such as 2-homopiperidin-1-ylethoxy or 3-dimethylaminopropoxy), the reaction of a compound of the Formula I wherein $R^1$ is a halogeno-substituted (1–6C) alkoxy group with a heterocyclyl compound or an appropriate amine;

(d) for the production of those compounds of the Formula I wherein an $R^1$ group contains a (1–6C)alkoxy or substituted (1–6C)alkoxy group or a (1–6C)alkylamino or substituted (1–6C)alkylamino group, the alkylation of a quinoline derivative of the Formula I wherein the $R^1$ group contains a hydroxy group or a primary or secondary amino group as appropriate;

(e) for the production of those compounds of the Formula I wherein $Z^1$ is a SO or $SO_2$ group, wherein an $R^1$ or $R^3$ substituent is a (1–6C)alkylsulphinyl or (1–6C)alkylsulphonyl group or wherein an $R^1$, $R^3$ or $R^{14}$ substituent contains a SO or $SO_2$ group, the oxidation of a compound of the Formula I wherein $Z^1$ is a S group or wherein an $R^1$ or $R^3$ substituent is a (1–6C)alkylthio group or wherein an $R^1$, $R^3$ or $R^{14}$ substituent contains a S group as appropriate;

(f) the reaction of a compound of the Formula VI

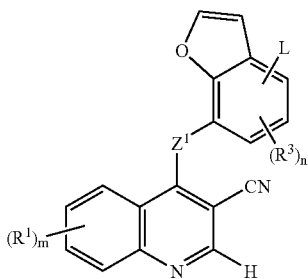

wherein L is a displaceable group and m, $R^1$, $Z^1$, n and $R^3$ have any of the meanings defined in claim 1 except that any functional group is protected if necessary, with a compound of the Formula VII $HZ^2\text{-}R^{14}$        VII wherein $Z^2$ is a C≡C or $C(R^{13})$=$C(R^{13})$ group and $R^{13}$ and $R^{14}$ have any of the meanings defined in claim 1 except that any functional group is protected if necessary, whereafter any protecting group that is present is removed by conventional means;

(g) for the production of a compound of the Formula I wherein $R^{14}$ is a carboxy group, the cleavage of a compound of the Formula I wherein $R^{14}$ is a (1–6C) alkoxycarbonyl group;

(h) the reaction of a compound of the Formula I wherein $R^{14}$ is a carboxy group with an appropriate amine to form a further compound of the Formula I wherein $R^{14}$ is a carbamoyl, N-(1–6C)alkylcarbamoyl, N,N-di-[(1–6C)alkyl]carbamoyl or heterocyclylcarbonylamino group; or (i) a coupling reaction of a compound of the Formula VIII

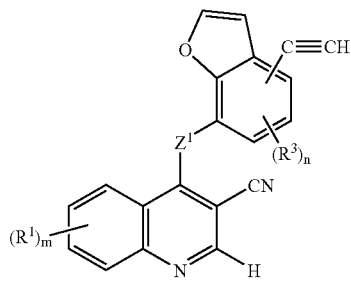

wherein m, $R^1$, $Z^1$, n and $R^3$ have any of the meanings defined in claim 1 except that any functional group is protected if necessary, with a compound of the Formula IX

L-$R^{14}$        IX wherein L is a displaceable group and $R^{14}$ has any of the meanings defined in claim 1 except that any functional group is protected if necessary, whereafter any protecting group that is present is removed by conventional means;

and when a pharmaceutically-acceptable salt of a quinoline derivative of Formula I is required it may be obtained using a conventional procedure.

9. A pharmaceutical composition which comprises a quinoline derivative of the Formula I, or a pharmaceutically-acceptable salt thereof as defined in claim 1 in association with a pharmaceutically-acceptable diluent or carrier.

* * * * *